US009261445B2

(12) United States Patent
Peters et al.

(10) Patent No.: US 9,261,445 B2
(45) Date of Patent: Feb. 16, 2016

(54) SYSTEM FOR MEASURING GOLF SWING PARAMETER DATA ON IMPACT OF A GOLF CLUB FACE WITH A TARGET SURFACE

(71) Applicants: Garry Peters, West Vancouver (CA); Peter Klein, Langley (CA)

(72) Inventors: Garry Peters, West Vancouver (CA); Peter Klein, Langley (CA)

(73) Assignee: Garry Peters, West Vancouver, British Columbia (CA)

( * ) Notice: Subject to any disclaimer, the term of this patent is extended or adjusted under 35 U.S.C. 154(b) by 0 days.

(21) Appl. No.: 14/300,650

(22) Filed: Jun. 10, 2014

(65) Prior Publication Data

US 2015/0068274 A1 Mar. 12, 2015

Related U.S. Application Data

(63) Continuation-in-part of application No. 13/473,741, filed on May 17, 2012, now Pat. No. 8,808,101.

(51) Int. Cl.

| | |
|---|---|
| *A63B 69/36* | (2006.01) |
| *G01N 3/30* | (2006.01) |
| *G09B 19/00* | (2006.01) |
| *A63B 69/32* | (2006.01) |
| *A63B 71/06* | (2006.01) |
| *A63B 24/00* | (2006.01) |
| *A63B 71/02* | (2006.01) |

(52) U.S. Cl.
CPC *G01N 3/30* (2013.01); *A63B 69/32* (2013.01); *A63B 69/3623* (2013.01); *A63B 71/0622* (2013.01); *G09B 19/0038* (2013.01); *A63B 2024/0037* (2013.01); *A63B 2024/0043* (2013.01); *A63B 2071/024* (2013.01); *A63B 2071/0625* (2013.01); *A63B 2071/0694* (2013.01); *A63B 2207/02* (2013.01); *A63B 2209/00* (2013.01); *A63B 2209/10* (2013.01); *A63B 2209/14* (2013.01); *A63B 2210/50* (2013.01); *A63B 2220/13* (2013.01); *A63B 2220/30* (2013.01); *A63B 2220/40* (2013.01); *A63B 2220/53* (2013.01)

(58) Field of Classification Search
CPC .... A63B 57/00; A63B 53/00; A63B 69/3632; A63B 69/0074
See application file for complete search history.

(56) References Cited

U.S. PATENT DOCUMENTS

| | | | |
|---|---|---|---|
| 3,874,664 A | 4/1975 | Faurot et al. | |
| 5,553,860 A | 9/1996 | Zelikovich | |
| 5,626,526 A | 5/1997 | Pao et al. | |
| 5,908,194 A | 6/1999 | Schachter et al. | |
| 6,244,973 B1 | 6/2001 | Eichelberger | 473/226 |
| 6,254,492 B1 | 7/2001 | Taggett | 473/219 |

(Continued)

*Primary Examiner* — David L Lewis
*Assistant Examiner* — Shauna-Kay Hall
(74) *Attorney, Agent, or Firm* — Matthew J. Lattig; Charter IP, LLC

(57) ABSTRACT

A system for measuring golf swing parameter data on impact of a club face of a user's golf club with a target surface includes an absorber bag having a front facing surface with target image thereon for receiving an impact of the user's club face therewith, an anchor frame to which the bag is attached thereto, and an electronics module removably attachable to the anchor frame. The system further includes a plurality of shock mounts positioned between the absorber bag and anchor frame, and at least one accelerometer in electrical communication with the electronics module and arranged on a rear surface of the bag that measures acceleration upon impact of the club face with the absorber bag, providing a signal that is converted by the electronics module into golf swing parameter data for display to the user.

20 Claims, 13 Drawing Sheets

(56) References Cited

U.S. PATENT DOCUMENTS

| | | |
|---|---|---|
| 6,441,745 B1 | 8/2002 | Gates |
| 7,691,003 B2 | 4/2010 | Munshi |
| 2003/0216228 A1 | 11/2003 | Rast ............................ 482/84 |
| 2004/0063509 A1* | 4/2004 | Shioda ......................... 473/139 |
| 2008/0098797 A1* | 5/2008 | Considine et al. ............ 73/12.09 |
| 2008/0125293 A1 | 5/2008 | Ng ................................ 482/84 |
| 2008/0146362 A1 | 6/2008 | Cui .............................. 473/139 |
| 2011/0111872 A1 | 5/2011 | Ishii ............................. 473/219 |
| 2011/0151984 A1* | 6/2011 | Prater .......................... 473/143 |

* cited by examiner

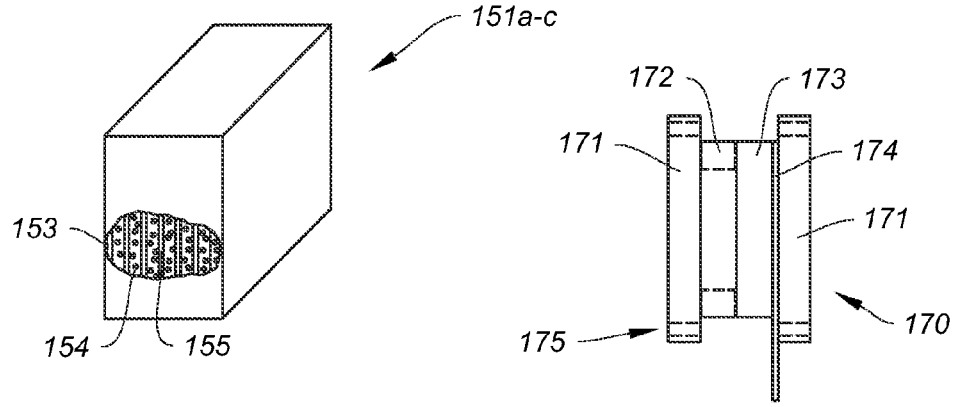
FIG. 7
FIG. 9
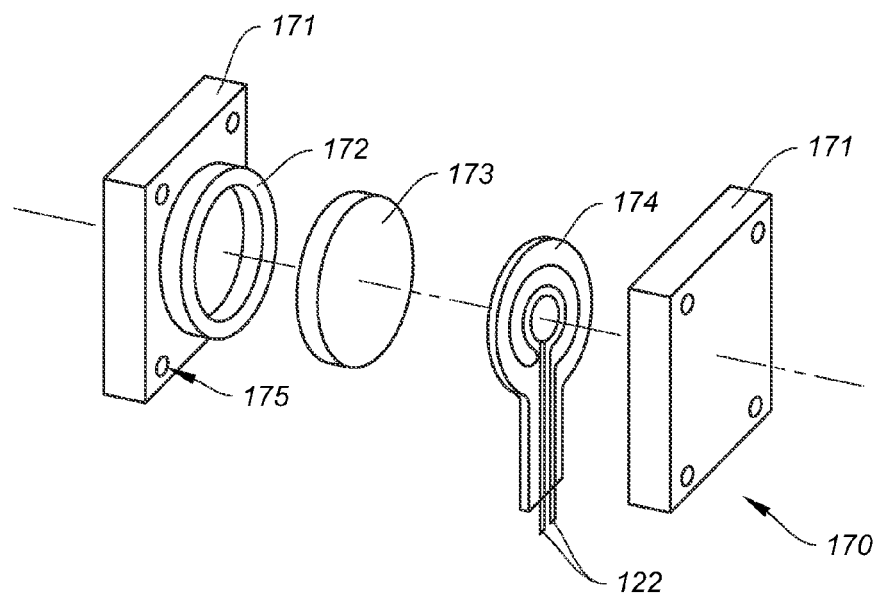
FIG. 8

SYSTEM FOR MEASURING GOLF SWING PARAMETER DATA ON IMPACT OF A GOLF CLUB FACE WITH A TARGET SURFACE

CROSS-REFERENCE TO RELATED APPLICATION

The present application claims the benefit under 35 U.S.C. §120 of U.S. patent application Ser. No. 13/473,741, filed May 17, 2012, pending, the entire contents of which is hereby incorporated by reference herein.

BACKGROUND

1. Field

Example embodiments in general relate to a system for measuring golf swing parameter data upon impact of a golf club face with a target surface.

2. Related Art

In golf, one of the most important aspects of improving the golf swing is to maximize the force of the impact with the ball. There are numerous techniques and training devices on the market to teach techniques for improving the general swinging motion of the golfer, yet there is not a product to assist the golfer in measuring the actual force of their swing upon impact or contact with the ball.

One popular device on the market that is used to teach golfers to learn proper body mechanics for maximizing the impact of the club face hitting the ball is the "Impact Bag Golf Swing Training Aid" offered at PracticeRange.com. Although this product offers to help find the correct swing path at impact, it has no means to actually measure the impact of the swing, i.e., the force imparted on the bag, upon contact between the golf club face and the impact bag.

An apparatus that can measure the impact of the club or club face with a static apparatus, and the ability to immediately communicate this actual impact data of the swing to the golf trainer and student would provide valuable information in order to improve the technique and mechanics of the golf swing. Therefore, a product that has the capability to convey the impact data of the swing on contact of the club face with the static apparatus during a training session may offer a unique and valuable contribution to the purpose of improving the student's golf skills.

SUMMARY

An example embodiment is directed to a system for measuring golf swing parameter data on impact of a club face of a user's golf club with a target surface. The system includes an absorber bag having a front facing surface with a target image thereon for receiving an impact of the user's club face therewith, an anchor frame to which the bag is attached thereto, and an electronics module removably attachable to the anchor frame. The system includes a plurality of shock mounts positioned between the absorber bag and anchor frame, and at least one accelerometer in electrical communication with the electronics module and arranged on a rear surface of the bag that measures acceleration upon impact of the club face with the bag, providing a signal that is converted by the electronics module into golf swing parameter data for display to the user.

Another example embodiment is directed to an absorber bag for measuring golf swing parameter data upon impact therewith with a club face of a user's golf club. The absorber bag includes an outer construction composed of a plurality of resilient panels arranged in a generally cubic shape with a front facing surface with a target image thereon for receiving the user's club face thereto for impact therewith, an electronics module, and an interior. The interior includes a plurality of alternating layers of fabric and open foam cell in adjacent stacked relation arranged behind the front facing surface as a front section of the interior, a frame as a rear section of the interior, and one or more accelerometers in electrical communication with the electronics module and positioned on the frame. The one or more accelerometers measure acceleration upon impact of the club face with the bag, providing signals that are converted by the electronics module into golf swing parameter data for display to the user.

Another example embodiment is directed to a system for measuring golf swing parameter data on impact of a club face of a user's golf club with a target surface. The system includes an absorber bag having a front facing surface for receiving an impact thereon with the club face, the absorber bag anchored directly to a ground surface so as to be fixed in place, and so the front facing surface is impacted by the club face at a bottom of a downswing of the club by the user, and at least one accelerometer that measures acceleration upon impact of the club face with the front facing surface. The system includes a processor connected to the at least one accelerometer for receiving the acceleration data and determining golf swing parameter data related to the impact.

BRIEF DESCRIPTION OF THE DRAWINGS

Example embodiments will become more fully understood from the detailed description given herein below and the accompanying drawing, wherein like elements are represented by like reference numerals, which are given by way of illustration only and thus are not limitative of the example embodiments herein.

FIG. 7 is a cross-sectional view taken across A-A of pillow 151 in FIG. 6 to illustrate material components thereof in more detail.

FIG. 8 is an exploded view of a velocity sensor 170 from FIG. 6 to describe the constituent components thereof in more detail in accordance with one embodiment.

FIG. 9 is a side view of the velocity sensor 170.

DETAILED DESCRIPTION

As to be set forth more fully below, the example embodiments in general are directed to a system for measuring golf club parameter data on impact of a club face of a user's golf club with a target surface, and to an impact bag for measuring parameter data upon impact therewith with a club face of a user's golf club.

Figure 1:
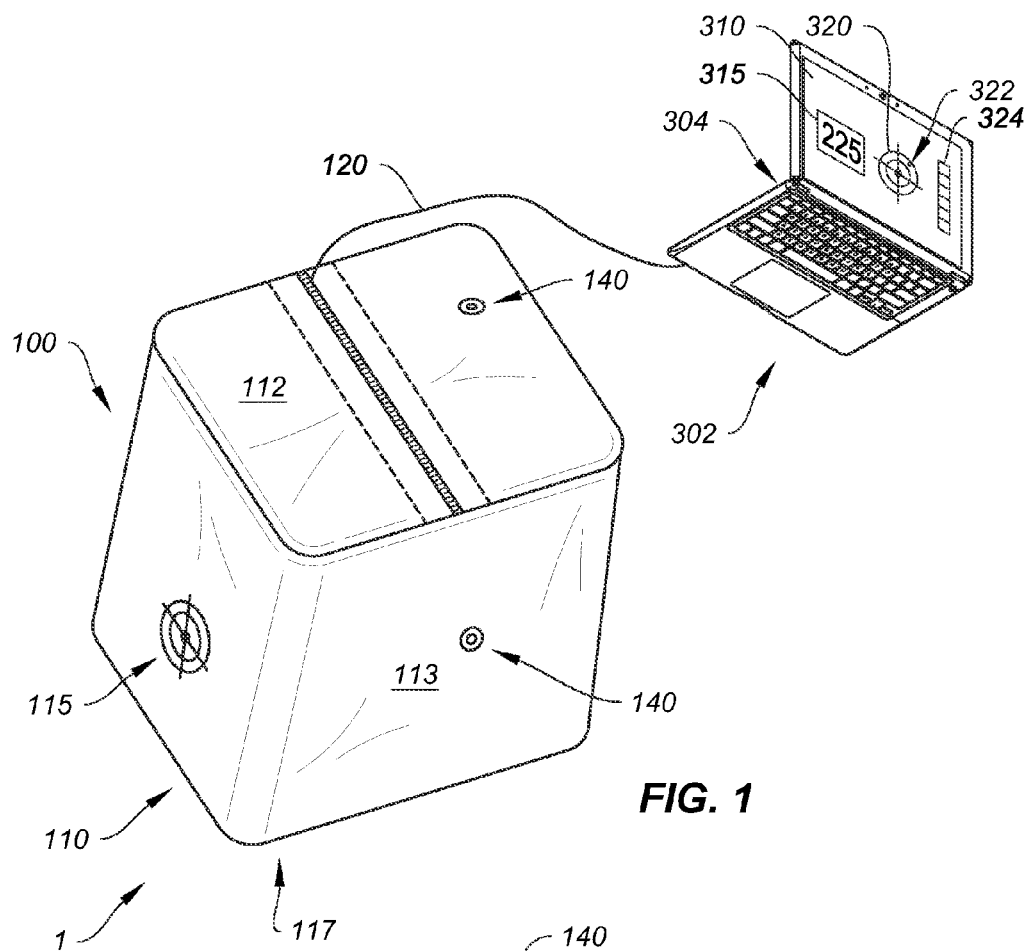
FIG. 1 is a perspective view of system for measuring parameter data upon impact with an impact bag of the system therewith with a club face of a user's golf club.
Figure 2:
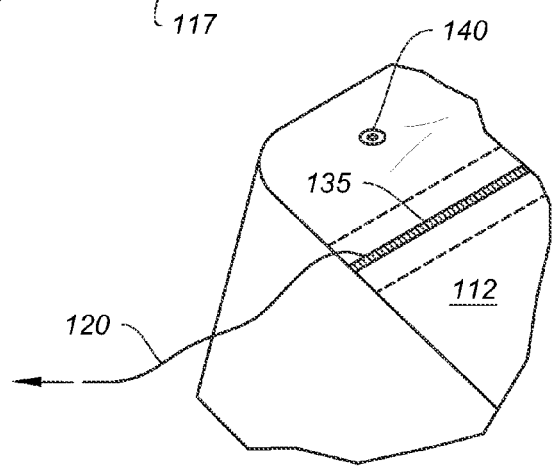
FIG. 2 is a partial top view of the impact bag of FIG. 1.
Figure 3:
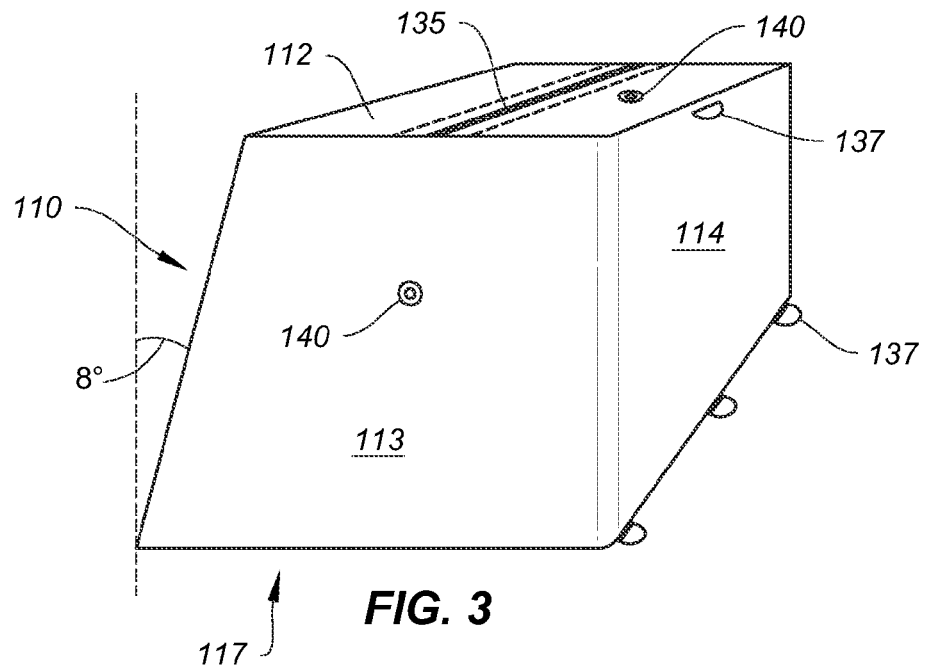
FIG. 3 is a left-side sketch view of the impact bag to illustrate additional components thereof.
Figure 4:
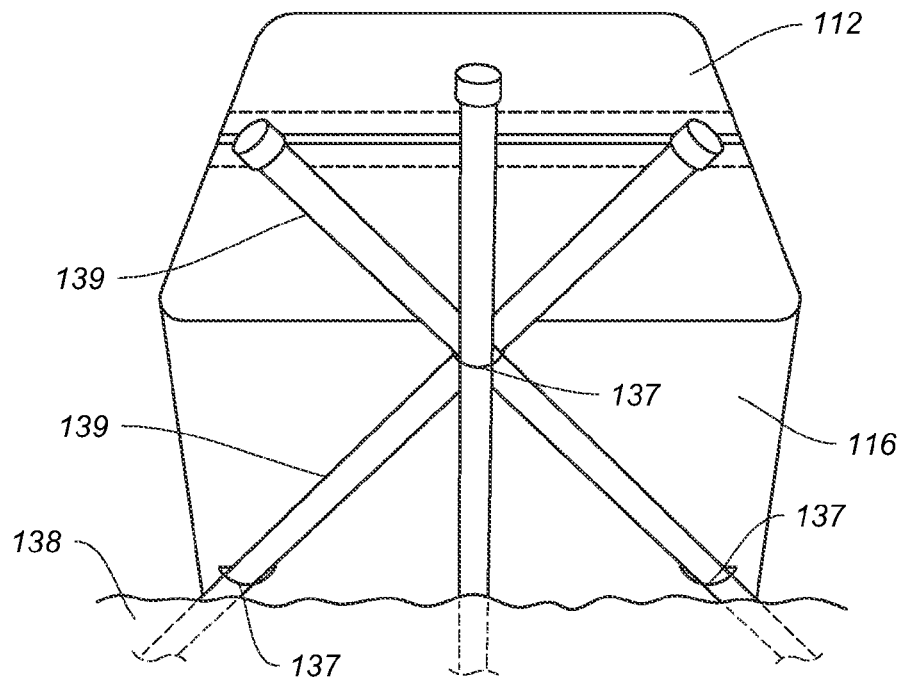
FIG. 4 is an upper rear view of the impact bag to illustrate the use of stakes for securing the bag to a ground surface.

FIG. 1 is a perspective view of system for measuring parameter data upon impact with an impact bag of the system therewith with a club face of a user's golf club; FIG. 2 a partial top view of the impact bag of FIG. 1; FIG. 3 a left-side sketch view of the impact bag to illustrate additional components thereof; FIG. 4 an upper rear view of the impact bag to illustrate the use of stakes for securing the bag to a ground surface; and FIG. 5 a front plan view of the impact bag connected to a computer illustrating impending impact with the target surface by a club face.

Referring to FIGS. 1-5, there is shown and described a system and apparatus for measuring parameters related to a golf swing upon impact of a golf club face with a target surface. In general, the system 1 includes an impact bag 100 operatively connected to or in communication with a processor 304 with a remote or local display 310. The processor 304 is connected to a plurality of sensors (not shown) within the impact bag 100 via a cable 120 for receiving data therefrom. The display 310 communicates with or otherwise is configured under processor 304 control to display data to the user.

In an example and as to be further described in detail hereafter, upon impact of the golf club face 200 with the front facing target surface 110 (hereafter "front surface 110") of the bag 100, such as at a target area image 115 on surface 110, the embedded sensors measure data on impact that is transmitted to the processor 304 for conversion into golf club 200 parameter data that is visually represented on the display 310 for evaluation by the user and or a trainer. In the illustrated example of FIG. 1, this parameter data displayed to the user may be how hard the user struck the impact bag or club head speed; i.e., a "hit strength" value or number indicated as an LED number in cell 315 on display 310, as well as an accuracy indication—an indication of how close to the target image 115 the club face 200 landed, i.e., a "hit location" parameter, shown as by example, an LED direction light reading 322 on a target image icon or cell 320 on display 310, which shows the actual hit location relative to the target point or reference point.

Optionally, display 310 can include an LED bar graph 324. The LED bar graph 324 may be provided to intuitively show the hit strength by height (if oriented vertically) or length (if oriented horizontally) in an illuminated column. After a low hit strength, a few bars (or none at all) may be illuminated, indicating a weaker hit. After a strong hit many or all bars light up. As an example, the bar graph could be divided into 10 LED increments which could be calibrated at 10 lbs of force for a dynamic display range of 100 lbs. Additionally, the LED bar increments or bar graph 324 may be color coded, for example the top LED(s) may be red, next few below may be orange, further below yellow, then green, and the bottom two elements may be blue. If only the blue ones light up, one doesn't need to count bars as it is immediately apparent that the hit didn't exceed 20 lbs of force. The display may be embodied as an LED, or similar such as Vacuum fluorescent, OLED, etc.

The impact bag 100 has a generally cubic shape with a front surface 110. The front surface 110 has an approximate 8 degree sloping angle downward from top to bottom. This angle is to approximate a line angle of a golf club as it sits on the ground.

The front surface 110 of the impact bag 100 is oriented at an angle (8 degrees). The reason is to encourage proper shaft lean at impact. Most golfers throw the club head at the ball and increase loft on the face of the club. Tour Professionals de loft the golf club, on average 4 to 6 degrees, and sometimes more. The low point of the swing is 3 to 4 inches in front of the ball. Accordingly, the design of the impact bag 100 encourages this downward strike and compression of the golf ball. All clubs are hit on the downswing except the driver.

The sloped front surface 110 may include a target image 115 printed thereon to guide the user to the target area. As discussed previously, the impact bag 100 may be part of a system, operatively attached to a processor, such as a computer system (PC, PDA, laptop, etc) running analytic software to analyze the measured data upon impact of the front surface 110 at target image 115 with a golf club face 200 and output a tangible result to the user/golfer, such as how hard the golfer struck the impact bag 100 (as a minimum level of impact measurement) an accuracy of the hit on the target image 115, i.e., hit strength and hit accuracy.

Figure 5:
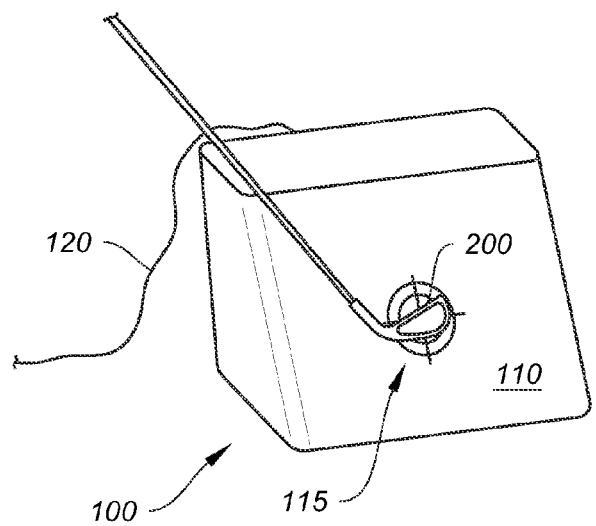
FIG. 5 is a front plan view of the impact bag connected to a computer illustrating impending impact with the target surface by a club face.

In FIGS. 1, 2 and 5, a wired configuration is shown, in which cable 120 connects one or more sensors placed behind the front surface 110 to a computing medium such as a PC or laptop via a suitable connection means, such as a USB port for example. This is only one configuration, as the impact bag 100 could be a standalone unit hooked up to a pressure gage, or configured for wireless communication to a remote computing device in other embodiments.

The bottom panel 117, top panel surface 112, back panel 116 and side panels 113 and 114 of the bag 100 may be constructed of a suitable resilient material such as reinforced vinyl, for example, although other resilient materials may be suitable such as leather, canvas and other synthetics. These panels 112, 113, 114, 116 and 117 may be attached by suitable stitching, sewing, bound seams, etc. In a particular example, panels 112, 113, 114 and 116 are double stitched for secure integrity and robustness against repeated hits.

The panel forming the front target surface 110 may be formed of an uncoated ballistic nylon material; i.e. a material that is used for bullet proof vests. In an example, an insert synthetic material (foam, plastic, rubber) may be placed in front of the panel forming the target front surface 110 so as to ensure that the 6 degree cant angle is preserved. The front panel may be sewn/stitched to the other panels to forms the bag shape. The filler or interior materials for the bag 100 will exhibit sound damping qualities and also add some heft/weight to the bag. Suitable filler material has soft, dense qualities that can withstand repeated impacts from a standard golf club; example materials may include terry cloth materials, foam rubber, etc. The interior components within impact bag 100 are described hereafter in more detail.

The impact bag includes a plurality of sensors embedded therein behind the front surface 110 and behind and around the target image 115. The sensors are configured to measure data upon impact of the club with the front surface 110 which provides the user parameter data from the impact. In an example, this data can include a rating indicating how hard the user struck the impact bag 100, as well as the accuracy of the hit at the desired target image 115.

The sensors have a robustness to be able to withstand repeated impacts to the target area image 115 on front surface 110. In general, the sensor technology provides the golfer measurable parameter data, such as a rating, as to how hard the golfer struck the impact bag 100 (as a minimum level of impact measurement). In an example, the sensors may be arranged in a particular location with materials on either side thereof; the specific orientation of which is described in detail hereafter.

The top panel surface 112 includes an opening or access 135 (shown by a zipper), to allow the user to adjust filler material and access the sensors therein. Instead of a zipper, a hook and loop overlap may be provided to secure the top panel flaps. Instead of the aforementioned arrangements, Velcro® may be used as a closing mechanism for access 135, as Velcro may be more robust and or durable than a zipper or hook and loop arrangement.

Additionally, there are included a plurality of ventilation holes 140 formed in the top and sides to allow pressure release. In an example, these may be formed of a metal material such as brass. The vent holes 140 help displace the air volume in the bag 100, creating less stress on the stitching and the covering material when hitting the bag 100 with a golf club, so as to preserve or extend the bag's life cycle.

As shown in FIGS. 3 and 4, a plurality of shaft or stake holders 137 are attached, three at the rear bottom surface and one centrally at the rear top. In an example these may be embodied as D-ring elements. These stake holders 137 may be employed to hold the impact bag 100 in place with stakes 139, spikes or other retaining elements securing the bag 100 into the ground surface 138. Since the bag 100 remains anchored, no adjustments are required after each hit.

Although not shown in the figures, the system and/or impact bag 100 may further include guiding plane sticks or alignment sticks that are secured to the impact bag to help the golfer with their swing plane. The plane sticks are designed for teaching the proper path on the downswing. The plane sticks are designed to help correct all the downswing path errors (Outside in; Inside out; etc.). In an example, these would be placed in front of the bag 100 on either side, parallel to the golfer's swing path to the target.

Figure 6:
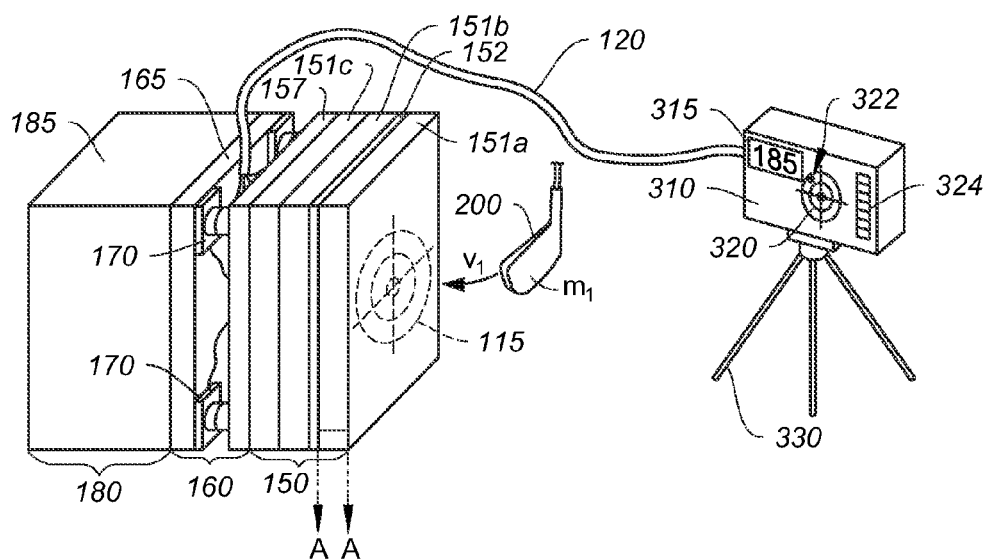
FIG. 6 is a perspective side view with the outer bag construction removed to illustrate interior components thereof in more detail.

FIG. 6 is perspective side view with the outer bag construction removed to illustrate interior components thereof in more detail. In order to provide feedback to user, such as a golfer and/or their instructor, as to speed of impact or club head speed (hit strength) and accuracy to hit a target spot with the club face 200 (hit accuracy), the system 1 and impact bag 100 thereof consider the following assumptions: a) the momentum of the head of the golf club is transferred to the golf ball (elastic impact $m_1 \times v_1 = m_2 \times v_2$; m=mass and v=velocity); b) the speed of the head of a golf club of a master or professional golfer (e.g., Tiger Woods) can be up to 125 mph; c) the impact bag 100 is anchored firmly to the ground and therefore absorbs the kinetic energy of the club head within itself; and d) the speed vector of the club face 200 at impact is parallel to the normal vector of a so called separator plate inside the bag 100.

Accordingly, for purposes of measurement, the system 1 and impact bag 100 employs force sensors (hereafter referred to as "velocity sensors 170"), conditions the signals thereof, processes the signals and displays a parameter value that represents speed at impact, as well as displays an indication of how close to the target the club head/club face 200 landed.

Referring now to FIG. 6, the exterior panels have been removed to illustrate interior components therein. The bag 100 is configured to handle two demands simultaneously: to absorb the kinetic energy of the club head $E = \frac{1}{2} mv^2$, and to translate the momentum, mv, into a force. To do so, the interior of impact bag 100 is arranged in three sections: a front section 150, a middle section 160, and a back section 180.

In general, the front section 150 includes a plurality of pillow elements 151a-c for energy absorption, so that the hit "feels right" (i.e., no shock, no bounce back, etc.). Additionally, there remains some residual kinetic energy left to move a separator plate 157 in the middle section 160. The middle section 160 includes the separator plate 157, which moves upon the front surface 110 being impacted by club face 200 (front pillow 151a shows target image 115 thereon to indicate the front) to compress a plurality of velocity sensors 170. Each velocity sensor 170 includes a spring element connected in parallel to a velocity proportional damper (not shown in FIG. 6) on the side facing away from the pillow side at pillow element 151c adjacent the separator 157. The velocity sensors 170 may be arranged in a set geometrical configuration to each other, for example, one in each corner of the separator plate 157, secured by fasteners between the separator plate 157 and a reaction plate 165 which constitute the middle section 160. The back section 180 comprises a mass 185 that is comparatively large as compared to the front and middle sections 150, 160, and is attached to the rear surface of reaction plate 165 by fastening means such as hooks, screws, etc., or force fit to plate 165 by Velcro®, adhesive, etc. The mass 185 can be a firm block of heavy material such as bags of lead shot, sand, etc., or a liquid in a tank. For liquid in a tank, a collapsible tank from flexible material may be used for compact storage and ease of transportation.

Accordingly, the middle section 160 carries the velocity sensors 170, which turn a force acting on each into a respective electrical signal. The velocity sensors 170 are placed at the four corners of separator plate 157 so as to be mechanically connected to the separator plate 157 towards the front section 150 and mechanically connected to the reaction plate 165 towards the back section 180.

A hit with the golf club face 200 of mass m1 touches first pillow 151a at a speed of v1 which represents momentum M1. The energy $E_1 = \frac{1}{2} m_1 \times v_1$ of the golf club face 200 hitting first pillow 151*a* gets partially absorbed in the front section 150 in such a way that the golf club 200 does not bounce back, but stops. The stopping motion is sought to feel similar as if the golf club face 200 had hit a golf ball.

However, the absorption characteristics of the front section 150 are selected so that some residual momentum of the front section 150 pillow elements 151*a-c*, force distribution plate 152, and separator plate 157 remains. This residual momentum compresses the velocity sensors in the middle section 160 due to the mass 185 in the back section 180 representing a mass much larger than the mass of the front section 150. In that respect, the mass of reaction plate 165 slightly increases the mass of the back section 185, and the mass of separator plate 157 becomes part of the mass of the front section. This arrangement sees the momentum M1 of the golf club face 200 being transferred to the front section 150 where the impact is mainly absorbed in a plastic deformation and partially conveyed in an elastic impact as a momentum $M2=m2 \times v2$, whereby m2 represents the combined masses of separator plate 157 plus pillow elements 151*a-c*. This momentum M2 now gets practically absorbed in the velocity sensors 170. The electrical signals from the velocity sensors 170 are carried by cable 120 or wireless means to display 310. The display 310 may be placed so that the parameters of interest, such as hit strength value at 315 and intuitively at 324, hit accuracy/hit location at 320/322, can easily be seen by the person training with the bag 100.

In order to absorb golf club hits in a manner described above, it is advantageous to use multiple thinner absorption pillow elements 151*a-c* of similar or equal construction rather than a single thick pillow. Additionally, a force distribution plate 152 of reasonably hard material may be inserted between pillow elements 151*a* and 151*b* in order to reduce a certain dependency of the strength indication from the surface area of the golf club face 200.

FIG. 7 is a cross-sectional view taken across A-A of pillow 151*a* in FIG. 6 to illustrate material components thereof in more detail. Each of pillow elements 151*a-c* may be constructed as described hereafter with respect to pillow element 151*a*. In FIG. 7, each pillow element 151*a-c* may be composed of alternating layers of open cell foam 154 with fabric layers 155 which are encased within a liner 153 of flexible and durable material. The compression and decompression of the open cell foam 154 forces air sitting in the pores of the foam 154 to be displaced and to pass through fabric layers 155. The friction and creation of turbulence of the air turns the kinetic energy of the moving air molecules into heat energy which dissipates into the environment.

In order to provide reasonably accurate and consistent hit strength indications, the absorption qualities of the pillow elements 151*a-c* as described either are constant or change in a known fashion. In fact, temperature can affect the spring qualities of the foam 154. Thus, the example embodiments envision placing one or more temperature sensors in the front section 150 and/or middle section 160 of the bag 100 (not shown in FIG. 6, but within the interior of one or more of the pillow elements 151*a-c*, separator plate 157 and or reaction plate 165 and electrically connected to cable 120). This allows an accounting and compensation for the effects of temperature on the spring and damping characteristics of the pillow elements and the velocity sensors 170. In an example, this compensation can either be done by electronic hardware compensation circuitry in processor 308, or by processing the signals of the force and temperature sensors digitally.

FIG. 8 is an exploded view of a velocity sensor 170 from FIG. 6 to describe the constituent components thereof in more detail in accordance with one embodiment, and FIG. 9 is a side view of the velocity sensor 170. Referring to FIGS. 8 and 9, the velocity sensor 170 is arranged between the separator plate 157 and reaction plate 165. The residual momentum M2 of the pillow elements 151*a-c* and separator plate 157 compresses the velocity sensor, and is the product of the mass of these elements and the velocity they move with. Therefore, this velocity v2 is to be measured by the velocity sensor 170.

As an example velocity sensor 170, commonly available in the industry include sensors which measure acceleration and force. If accelerometer sensors are employed, integrating their signals provides the associated velocity. Alternatively, by selecting a final geometry of viscoelastic foam pieces, desired values for a particular application can be obtained.

An example configuration may employ force sensing resistors, also called FSR's, which are commonly available and inexpensive. The FSR construct includes a thin layer of conductive foam between two electrodes. The amount of compressive force changes the conductance between the electrodes.

Given the sensor principles described above, one of many possible embodiments for velocity sensor is shown in FIGS. 8 and 9. Specifically, velocity sensor 170 may include mounting an FSR element 174, which includes electrical leads 122 which are connected to cable 120, onto a rigid mounting plate 171. This can be done by using an adhesive or glue or pressure sensitive double sided tape. Onto the free side of the FSR, a disc 173 of viscoelastic foam may be mounted in similar fashion. If fine tuning of the velocity sensor 170 calls for a softer spring element than disc 173 alone provides, then another piece of viscoelastic foam 172, here shown in the form of a donut, can be adhered to disc 173. Finally, another mounting plate 171 is adhered to the free side of donut-shaped disc 172, again using adhesives as described above. The mounting plates 171 may includes a plurality of bores 175 at corners thereof to fixedly couple the velocity sensor 170 via fastening means to both the separator and reaction plates 157, 165.

It is possible to mold part or all of the entire arrangement as described above in modern manufacturing technologies, such as by injection molding. Selecting the formulation of the viscoelastic material, which in an example may be polyurethane, in combination with the geometry of discs 172 and 173 provides stiffness and damping characteristics in such a way that they result in making use of the full dynamic range of the chosen FSR element 174 and yet prevent overloading the FSR element 174 within the expected velocity range of golf clubs hitting the impact bag 100.

Figure 10:
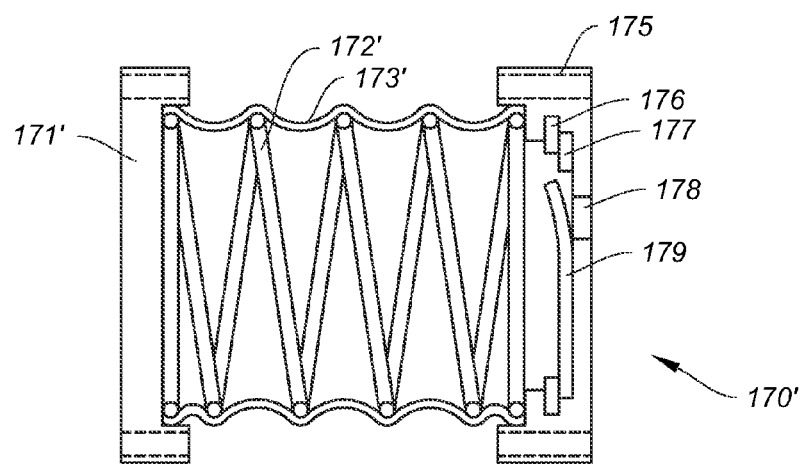
FIG. 10 is a side view of a velocity sensor 170' in accordance with another example embodiment.

FIG. 10 is a side view of a velocity sensor 170' in accordance with another example embodiment. In FIG. 10, velocity sensor 170' includes a coil spring 172' that is connected between mounting plates 171 and which is encased within a bellows-type hull 173'. The purpose of hull 173' is to form a substantially airtight chamber in conjunction with mounting plates 171. However, a hole 178 in mounting plate 171 in principle allows air passage outwards when the spring/bellows arrangement gets compressed and inwards upon decompression. The smaller the hole cross section, the higher the damping factor.

If a fast recovery time is desired the effective hole cross section should be small when the spring gets compressed and large during the decompression phase. This can be achieved with a seal 177, retained by retainer ring 176 against the inner wall of mounting plate 171. The seal 177 has a tongue-shaped flexible cutout 179 with a pin hole in line with the center of hole 178 which is much larger in cross section. The result is that air flowing inbound is much less restricted in comparison to air being expelled outbound upon compression. The arrangement illustrated in FIG. 10, when supplemented by sandwiching a FSR element 174 (not shown) between a mounting plate 171 and either separator plate 157 or reaction plate 165 can be a functional substitute for the arrangement shown in FIGS. 8 and 9, with the advantage of there being less change in spring and damping characteristics with temperature.

Figure 11:
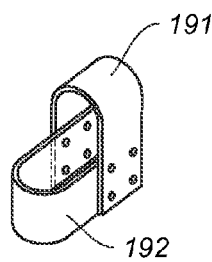
FIG. 11 is a perspective view of example leaf springs usable between the separator and backing plates in the middle section of the impact bag interior.
Figure 12:
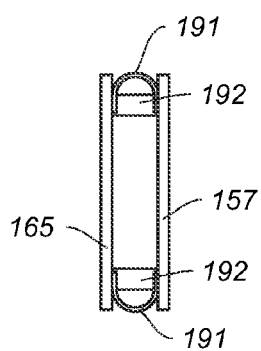
FIG. 12 is a side view of the separator and backing plates in the middle section of the impact bag interior with leaf springs installed.

FIG. 11 is a perspective view of example leaf springs usable between the separator and backing plates in the middle section of the impact bag interior; FIG. 12 is a side view of the separator and backing plates in the middle section of the impact bag interior with leaf springs installed; and FIG. 13 is a corner side view of the separator and backing plates in the middle section of the impact bag interior with leaf springs installed about a velocity sensor.

In practice, if the velocity sensors 170 are constructed from a plastic material such as foam polyurethane, any sustained force will see the plastic material creep. Such a sustained force can be inflicted by gravity when the bag 100 is tilted or lies face down instead of sitting upright. In the face down position the separation plate 157 and reaction plate 165 would be parallel to the ground and the velocity sensors 170 would be compressed. The effect of creep is that the spring rate of the velocity sensors 170 changes. This in turn adversely affects measurement accuracy.

Figure 13:
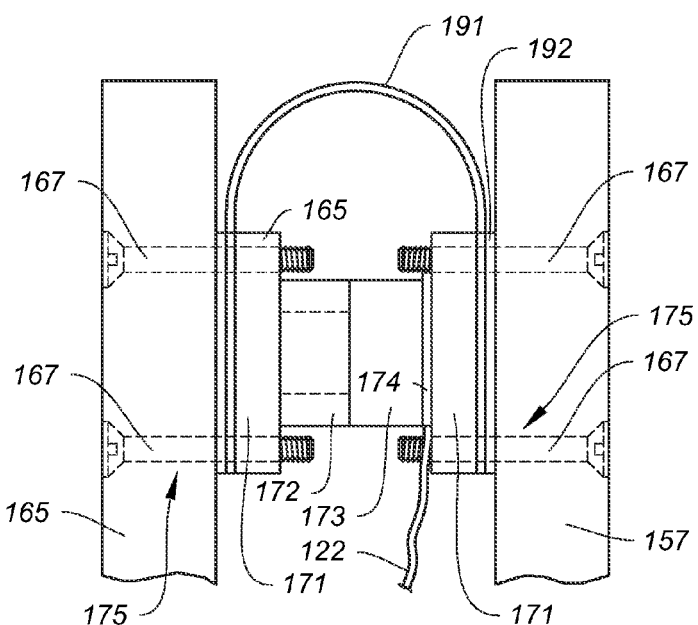
FIG. 13 is a corner side view of the separator and backing plates in the middle section of the impact bag interior with leaf springs installed about a velocity sensor.

Referring to FIGS. 11-13, and to reduce prolonged force exerted on the velocity sensors 170, additional metal springs can be employed. FIG. 11 shows an arrangement of two leaf sprigs 191, 192 with a 90 degree offset. The arrangement of double leaf springs 191, 192 placed in each corner and between separation plate 157 and reaction plate 165 allows the distance between these two plates to be easily affected by the impact from a golf club face 200, while at the same time in-plane shifting of separation plate 157 and reaction plate 165 is minimized due to the leaf springs 191 and 192 appearing much more stiff for such in-plane shifting.

As shown in FIGS. 12 and 13, leaf springs 191 and 192 are placed at the corners of separation plate 157 and reaction plate 165. Additionally, the bores 175 through which extend fasteners 167 are shown to connect the mounting plates 171 of the velocity sensor 170 between the separation plate 157 and reaction plate 165. Alternatively, other means of attachment, such as by snap fit engagement, slide on engagement, magnetic coupling, etc., may be employed.

Figure 14:
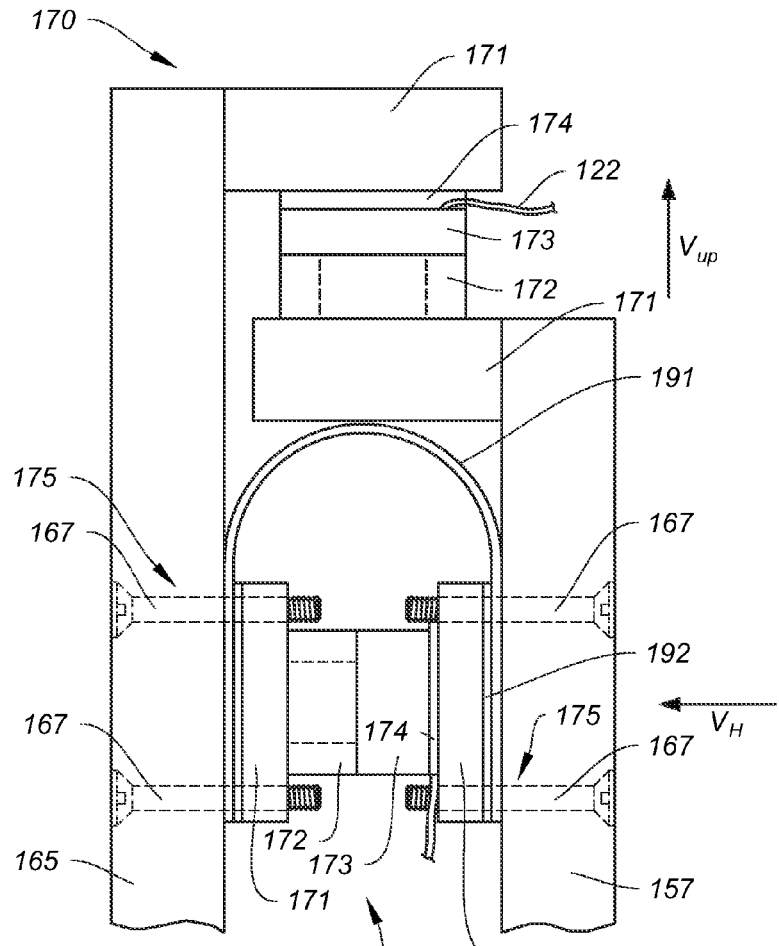
FIG. 14 is a partial side view of the separator and backing plates in the middle section of the impact bag interior with velocity sensors installed at each of a top and on a side edge thereof.
Figure 15:
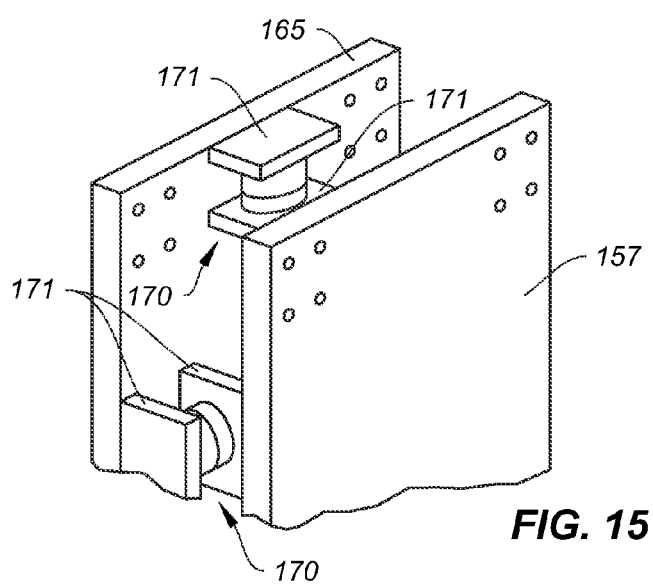
FIG. 15 is a partial upper perspective view of the separator and backing plates in the middle section of the impact bag interior with velocity sensors installed at each of a top and on a side edge thereof.

FIG. 14 is a partial side view of the separator and backing plates in the middle section of the impact bag interior with velocity sensors installed at each of a top and on a side edge thereof, and FIG. 15 is a partial upper perspective view of the separator and backing plates in the middle section of the impact bag interior with velocity sensors installed at each of a top and on a side edge thereof. Referring to FIGS. 14 and 15, the corner velocity sensors 170 are removed for purposes of clarity. Here, additional velocity sensors 170 are placed on top and the sides of plates 157 and 165 in order to measure the in-plane movement when the velocity vector of a hit is not parallel to the normal vector of separator plate 157, see for example vectors $V_{up}$, and $V_H$. The purpose is to determine a hit in addition to the hit location by computing the vector sum from the signals of all velocity sensors 170. A discussion of hit angle follows hereafter.

Figure 16:
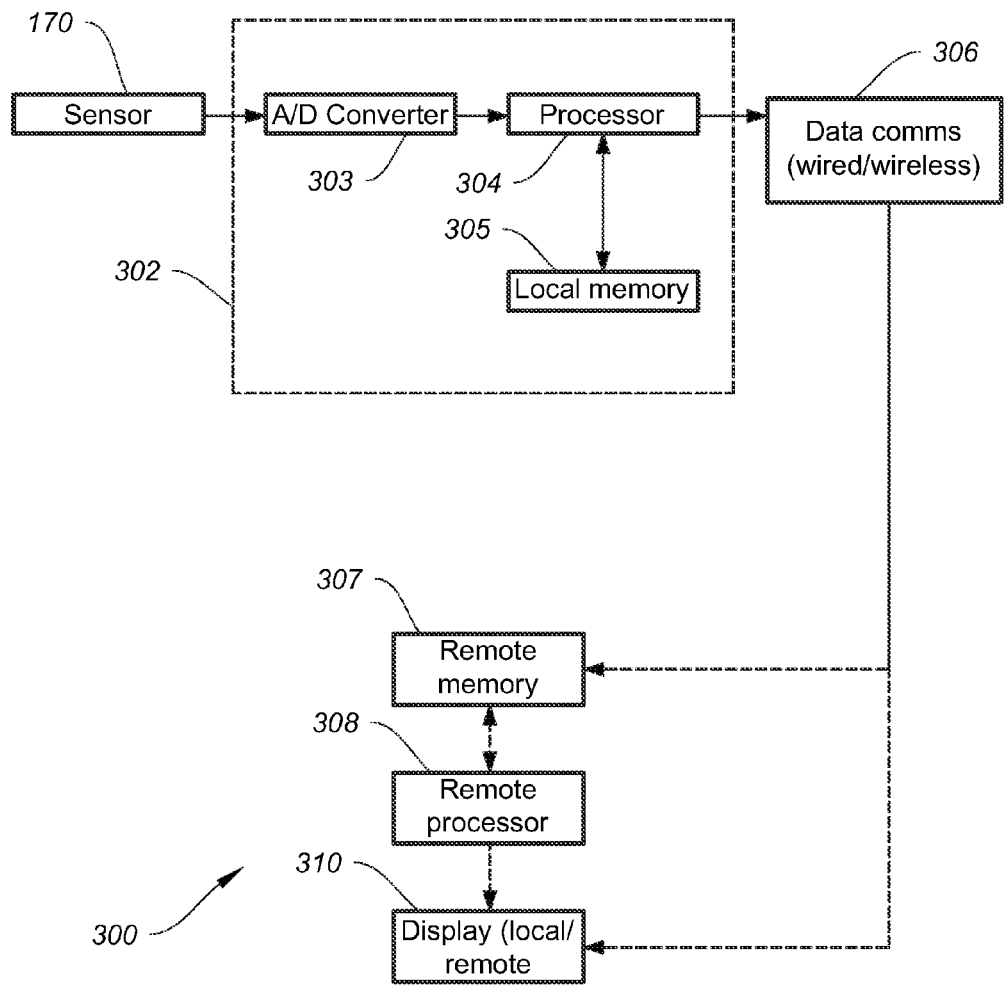
FIG. 16 is a block diagram illustrating the control electronics which processes the signals from the velocity sensors in accordance with the example embodiments.

FIG. 16 is a block diagram illustrating the control electronics which processes the signals from the velocity sensors in accordance with the example embodiments. Referring to FIG. 16, there is shown an example electronics system 300 for conveying the measurable data from the velocity sensors 170 for processing to be ultimately displayed as parameter data for a user (golfer hitting the impact bag 100, an instructor, etc.) to convey information on a local or remote display 310 as to how hard the user struck the impact bag 100 with the club face 200 or club head speed; i.e., a "hit strength" value indicated (as shown at element 315 in FIGS. 1 and 6), as well as an accuracy indication—an indication of how close to the target image 115 the club face 200 landed, i.e., a "hit location" parameter shown on display at 322 in FIGS. 1 and 6. Additionally, the example embodiments, as shown in FIGS. 14 and 15, envision the ability to determine a hit orientation. The hit location is determined with reference to a target location. From the target location each velocity sensor 170's location can be described as a vector with distance and orientation; this is described in more detail hereafter.

Each of the velocity sensors 170 generate an analog value via cable 120 that is converted by an associated A/D converter 303 in a processor 304 within a computing medium 302 (PC, laptop, tablet, PDA, smart phone, etc.) to a digital signal. Accordingly, for the four corner velocity sensors 170 there are four corresponding channels, one per velocity vector captured by each sensor 170. As for the hit angle determination, velocity sensors 170 arranged at the top and side edges (See FIGS. 14 and 15) also generate a channel reading. Each of the channel readings output from the A/D converter 303 may be processed by analytical software or firmware run under control of local processor 304 so as to determine the calculations for hit strength and hit accuracy. The readings and calculations or "hit parameters" determine by the software may be stored in local memory 305, and the calculations for hit strength and hit accuracy determined by the analytical software under processor 304 control transmitted via wired or wireless communication (data comms 306) for display on a local or remote display 310. The memory 305 enables a history log of the hit parameters to be stored. From this stored parameter data, calculations can be computed such as averages, trends, priorities to work on etc.

In the case of a local processor 304 and local display 310 connected to bag 100 as shown in FIG. 1, the parameter data calculated by processor 304 is displayed via a wired/wireless medium (data comms 306) onto a local display 310, such as is shown in FIGS. 1 and 6. In an alternative configuration, the local processor 304 could convey the data to an external processor 308, such as that of a tablet, PDA or smartphone, for display thereon, hence the dashed lines shown from data comms block 306 to remote control electronics at elements 307, 308 and 310. In a further alternative, the processor 304 with ADC 303 and associated local memory 305 could be embedded in the bag 100, with a remote display 310 connected via wired/wireless means (data comms 306).

Figure 17A:
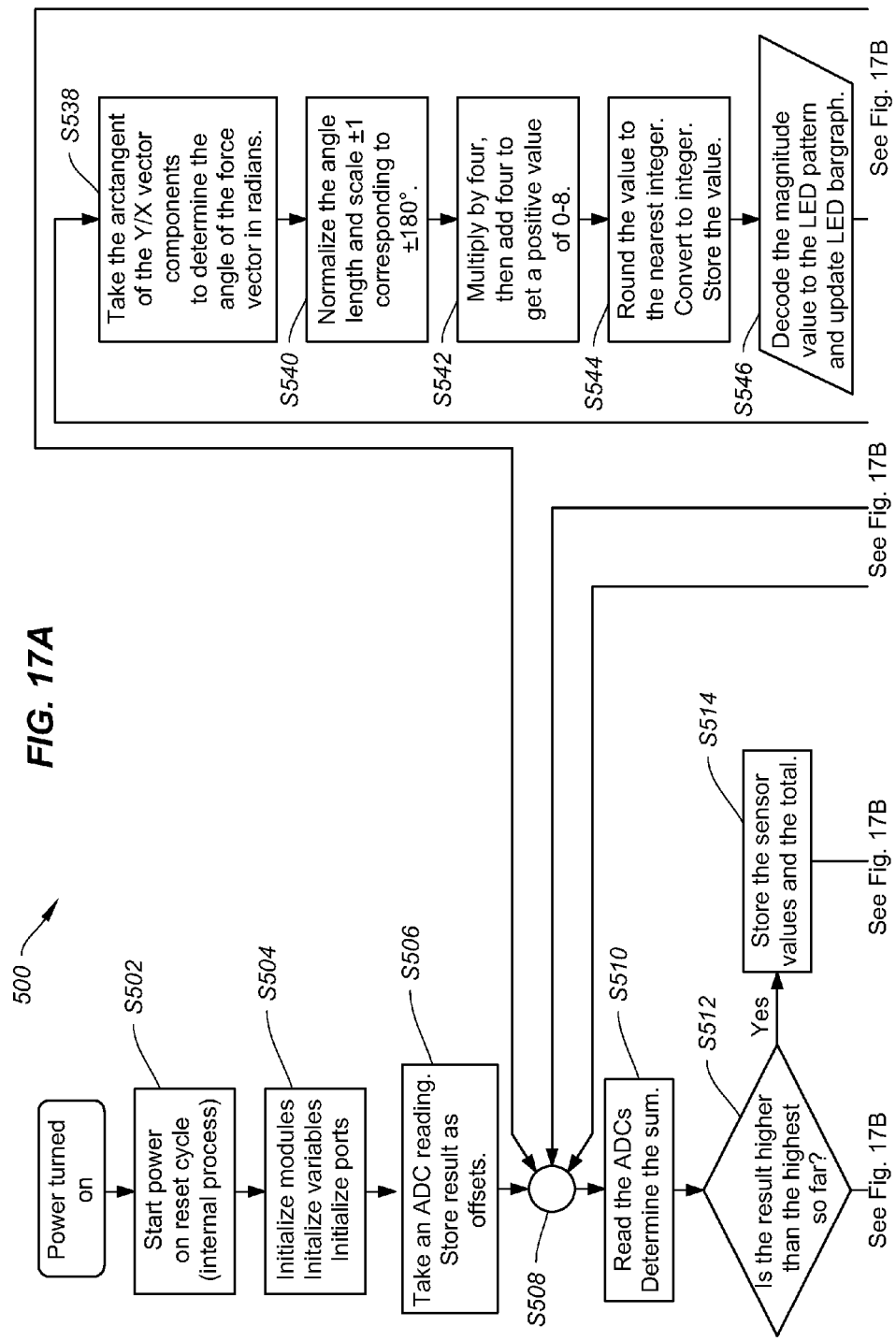
FIGS. 17A and 17B depict a flow diagram to illustrate processing calculations for the parameter data displayed to the user in accordance with the example embodiments.
Figure 17B:
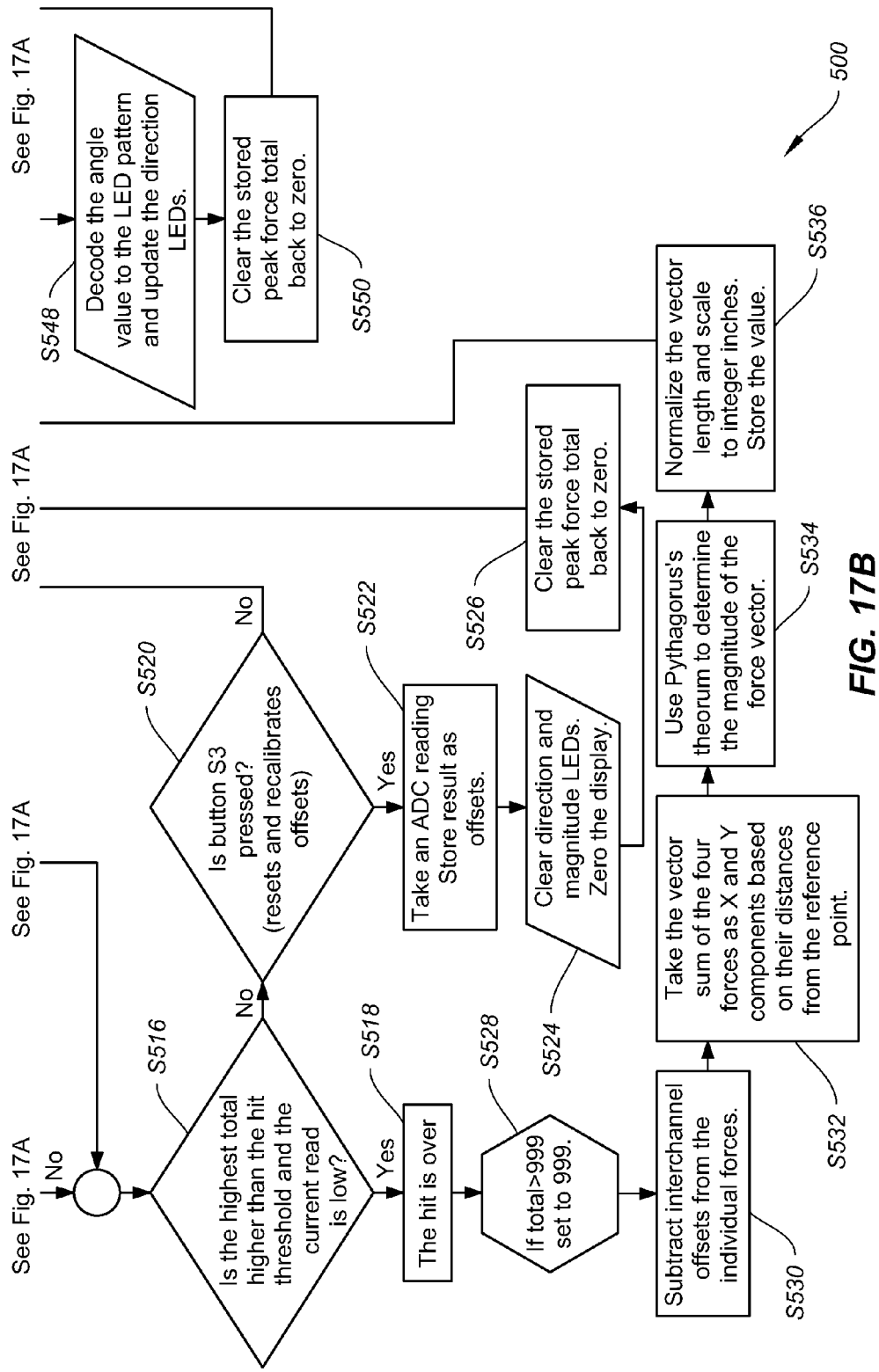

FIGS. 17A and 17B depict a flow diagram to illustrate processing calculations for the parameter data displayed to the user in accordance with the example embodiments. In particular, functional operations performed by the analytical software or firmware under control of processor 304/308 are described in order to determine the hit strength and hit accuracy information that is displayed to the user after an impact of the golf club face 200 with the target image 115 on the front surface 110 of bag 100.

Referring to FIG. 17A, the basic methodology 500 after power on includes an initial reset cycle (S502) and initialization procedures (S504) for the modules, variables and ports associated with each velocity sensor 170. Using microprocessor circuitry or a PSOC (Programmable System On Chip) involves working with timers, counters, amplifiers, etc. Upon applying power they hold random values of time, numbers, gain value etc. and get initialized to defined start values at S504. Initial ADC readings from the A/D converters 303 (as idle) are taken (S506) and stored as offsets, to get a baseline or reference prior to the hit.

The function at S508 represents impact of the golf club face 200 with the impact bag 100 front surface 110. At S510, upon impact, the ADCs 303 corresponding to the channels are read, one per velocity vector captured by each sensor 170, and a sum of the velocity vectors is computed. This sum is used to determine both the hit location and hit accuracy information that is displayed on display 310.

In the example embodiments, each velocity sensor 170 employs an FSR element 174. Each FSR element may be set at an example 20 lbs per sensor. This provides a maximum reading per sensor which is being read by an A/D converter of a given size, so for an 8 bit ADC 303, a maximum theoretical value would be 255 at the strongest hit. Of course, sensors 170 of different ratings and ADC's of different configurations could be used.

The impact bag 100 in the example embodiments has been configured so that a hit at 200 km/h (124 mph) with a certain mass right at the center between all four corner velocity sensors 170 produces a value of 63 at each sensor 170, for a total hit strength value on display 310 as 249. Thus, if only one sensor 170 was hit dead-on it would read 249 as well. Thus, the hit strength is determined by summing the values of the velocity sensors 170.

Hit location and hence hit accuracy is determined with reference to a target location. From the target location each sensor's location can be described as a vector with distance and orientation. The force reading of each sensor gets multiplied with its location vector, which gives each vector a "weight". The vector sum over all sensors gives the orientation, distance and hit strength. The following simplified examples aid in understanding the calculations for hit strength and hit accuracy/location.

EXAMPLES

With sensors 170 at the four corners between plates 157 and 165, the reference point is at the center between the sensors 170, e.g., the target image 115. Imagine a cartesian coordinate system with the origin at the target location. The distances can be normalized so as to describe the top right (TR) sensor location as (1,1), meaning x=1 and y=1. The top left (TL) sensor would be at (−1,1), the bottom left (BL) at (−1, −1), and the bottom right (BR) at (−1,1).

Thus, a dead center full strength hit could be described by following TABLE 1:

TABLE 1

DEAD CENTER, FULL STRENGTH

| Sensor | x | y | Magnitude |
|---|---|---|---|
| sensor TR | 63 | 63 | 63 |
| sensor TL | −63 | 63 | 63 |
| sensor BL | −63 | −63 | 63 |
| sensor BR | 63 | −63 | 63 |
| Total: | 0 | 0 | 249 |

Accordingly, for a full strength, dead center hit, x=0/249=0, y=0/249=0; thus location is (0,0), magnitude 249.

The following TABLE 2 is for a full strength hit, but off-center (top left):

TABLE 2

TOP LEFT, FULL STRENGTH

| Sensor | x | y | Magnitude |
|---|---|---|---|
| sensor TR | 0 | 0 | 0 |
| sensor TL | −249 | 249 | 249 |
| sensor BL | 0 | 0 | 0 |
| sensor BR | 0 | 0 | 0 |
| Total: | −249 | 249 | 249 |

Accordingly, for a full strength, top left hit, x=−249/249=−1, y=249/249=1; thus location is (−1,1), and magnitude is 249.

The following TABLE 3 is for impact with bag 100 in the middle of first quadrant, but with ¼ maximum strength:

TABLE 3

MIDDLE QUADRANT, ¼ FULL STRENGTH

| Sensor | x | y | Magnitude |
|---|---|---|---|
| sensor TR | 42 | 42 | 42 |
| sensor TL | −5 | 5 | 5 |
| sensor BL | −12 | −12 | 12 |
| sensor BR | 10 | −10 | 10 |
| Total: | 35 | 25 | 69 |

Accordingly, for a ¼ strength, middle quadrant hit, x=35/69=0.5, y=25/69=0.36; thus location is (0.5, 0.4), and magnitude is 69.

Referring now to the flowchart which extends across both FIGS. 17A and 17B, after the readings of sensors 170 are taken and sum of the vectors is determined at S510, it is determined whether the result is higher than the highest result (S512). If YES, the sensor values and sum are stored (S514) in memory 305; otherwise a determination is made as to whether the highest total exceeds a hit threshold and current read is low at S516. If YES, the hit is determined over (S518). If NO, a query is made at S520 as to whether an "S3" button at display 310 is pressed or not to reset and recalibrate the offsets (this may also be done by re-booting the computer 302). If the highest total is below the hit threshold and the offsets have not been reset/recalibrated (output of S520 is NO), the process returns to step S508, awaiting a next impact. Otherwise, the ADCs 303 are read at S522, the direction and magnitude LEDs on display 310 are cleared (elements 315 and 322/324 in FIGS. 1 and 6) at S524, and the stored peak force total is reset to zero at S526.

Accordingly, S508 to S516 and back through at S520 represent a loop. When the golf club face 200 hits the bag 100, the sensors 170 register a rising and then falling force over time. The time is short, on the order of milliseconds. To determine the impact velocity of a hit, the software is seeking the peak force value that each sensor 170 reads. Going through the loop between S508 to S516 and back through S520 many times during these few milliseconds, the rising numbers coming from the ADCs are detected and stored in memory 305 as long as they are rising; this is done at S514. When the numbers start falling this is sensed at S518 to break out of the above mentioned loop, meaning that the peak has been detected and for the purpose of calculating the golf data parameters (hit strength, hit accuracy/location, and hit orientation if edge sensors 170 are installed as shown in FIG. 15) the hit is considered over.

Once the hit is determined over at S518, then an integer value of the sum is set to 999 if the highest total exceeds 999

(S528). A hit that is stronger than the strongest anticipated hit can theoretically occur. The display 310 in the example embodiment is limited to three digits. To avoid showing misleading numbers for an exceedingly strong hit the displayed value is then artificially set to 999 by S528.

If the peak values as delivered by the ADCs 303 were used "as is", they would contain an error because the bag 100's contents shift slightly every time the bag 100 is put into place and the sensors 170 give some reading although no hit is imparted on the bag. Therefore, right at the beginning and prior to the hit at S508 these "idle" numbers are captured from the ADC 303s at S506. In S530 the "idle" numbers (interchannel offsets) are subtracted from the individual peak force values to achieve a fairly good representation of the actual impact velocity that each sensor 170 reads. Now the software is prepared to determine the golf data parameters: hit strength, hit location and if so equipped with edge-mounted velocity sensors 170, hit orientation. This computation begins at S532.

The computation of the vector sum follows the explanation illustrated in simplified form in Tables 1-3. At S532, the vector sum of the four forces is converted into x,y components based on each x,y component's distance from the reference point (S532). Pythagorus's theorem is employed (M=SQRT($x^2+y^2$) to determine the magnitude of the summed force vector at S534; this is the magnitude value that is to be displayed on display 310. The vector length is normalized and scaled to integer values and stored in memory 305 at S536, as shown at the bottom of FIG. 17B.

Referring briefly to FIGS. 1 and 6, and with reference to the LED direction light reading 322 on target image icon or cell 320 to display hit location and/or hit accuracy parameters for the user, the cell 320 in one example is configured in a 4-LED square (not shown in the FIG. 4 quadrants) to give a direction with reference to the center of the target symbol 115 on the bag 100's surface 110 in the plane of the front surface 110 of the bag 100 where the hit point is. The top left LED illuminated represents North-West of target center; the top right LED illuminated represents North-East of target center; top left and top right LEDs illuminated represents North of the target center. The South half works in like manner. The force vector computed in steps S532 to S536, with the object to determine the hit location, uses a cartesian coordinate system.

Referring again to FIG. 17B at S538, the vector is transformed to be represented in a polar coordinate system using angle and radius. The angle zero points East from the target center, which is displayed per the above by illuminating the LEDs top right and bottom right. With this simple location indicator, an angular resolution of about 45 degrees may be achieved, but the general principle is described. Accordingly, the normalized vector from S536 is employed to determine the hit accuracy information from the impact of the hit at S508. The arctangents of the Y/X vector components are used to determine the angle of the force vector at S538.

The computation in S538 delivers the arctangent value in radians. It would be possible to code a look-up table to determine which LED(s) are to be illuminated. This would be simple but not fast enough to sample the sensor values often enough to achieve the desired accuracy. If too slow, the peak value could be missed and, given the fast rise and fall characteristic of the hit, incur significant errors.

At S540 the arctangent value in radians gets divided by the number pi, which scales the 360 degree angle or 2 pi radians to a number between +1 and −1. It is also desirable to be able to quickly determine which of the 8 LED combinations, according to the 8 angles 45 degrees apart, is to be illuminated. In step S542, a quick transformation takes place to achieve this determination. After multiplying by 4 the numbers 1, 2, 3 and 4, these correspond to the angles in the northern half 0°, 45°, 90°, and 135°. The negative numbers carry on to sequence through 180°, 225°, 270°, and 315°. By adding 4, the negative numbers disappear and the positive numbers 1 through 8 now correspond to the sequential angles from 0° to 315°. The integer numbers cited above are special cases, albeit desired. To obtain them from the real numbers which result from the computations, these are rounded and converted to integer numbers in S544.

Again, with reference to the example embodiment, the direction of the hit location from the target center is displayed at 322 on the four LEDs which are representative by cell 320. The distance from the target center may alternatively be displayed by an LED bar graph where the magnitude value of the force vector in S534 is scaled to represent 1 inch per bar.

The magnitude value determined at S534 (in FIG. 17B), reflecting hit strength, is decoded to an LED pattern at S546 (see FIG. 17A) for display as a number in cell 315 on display 310. The integer value stored at S544 in FIG. 17A, representing an angle value reflecting hit location or accuracy, is decoded to an LED pattern for display (S548) (see FIG. 17B) as the LED direction light reading 322 on the target image icon or cell 320, such as is shown for example in FIGS. 1 and 6. Thereafter, the stored peak force total is reset to zero at S550, as shown on FIG. 17B. Before returning to the start point S508 to watch for the next hit the stored number representing the peak value of the present hit is set back to zero. This does not affect the parameters stored as hit strength and hit location.

Accordingly, hit strength and hit accuracy/location may be determined by system 1 as described above. The following describes in general terms how a hit orientation determination may be considered, with reference to FIGS. 14 and 15.

The golf club face 200 of the club moves on a trajectory in 3D space. Accordingly, it may also be desirable to determine also whether the golf club face 200 hit parallel to the normal vector VH of the front surface 110 of the bag 100, or, if not, at least to know the direction of the golf club trajectory at the point of impact.

Initially, a cartesian coordinate system can be assumed with the origin in the center of separator plate 157. The z-axis points in the direction of the normal vector VH of plate 157, with the x-axis pointing in the direction to the right Vup (see FIG. 15) and the y-axis pointing up. The club head face 200 strikes normally pillow 151a behind the front surface 110. However, for the purpose of this explanation the point where a club head 200 hits plate 157, referred to as the "hit point", is evaluated. The location of this hit point is determined by way of building the vector sum from the velocity sensors 170 in the corners (as previously described in the simple examples and in FIG. 17).

Next, the origin of the assumed coordinate system is moved to this hit point maintaining the orientation of the axes with respect to the edges of separator plate 157. The velocity vector of the club head 200 at the hit point has a component in the z-direction ("HPVz") that is measured with the velocity sensors 170 in the corners of plate 157 by summing up their signals (as described). The velocity vector of the club head 200 at the hit point also has a component in the x-y plane which is determined through the vector sum of the four velocity sensors 170 placed in the middle of the edges of plate 157 (see FIG. 15).

Building this vector sum follows the scheme explained for the determination of the hit location and yields a point in the x-y plane. This point in the x-y plane is called "HPVxy". Placing a cylinder coordinate system at the hit point, with its z-direction pointing towards reaction plate 165, and having its x-coordinate collinear with the x-axis of the cartesian coordinate system, permits describing the hit orientation through the vector from the hit point to the point with coordinates (HPVxy, HPVz).

To visualize this hit orientation vector (rather than hit angle) one could resort to computer generated graphics which show a 3D image. A simpler version may show the HPVxy component of the hit orientation vector as an arrow emanating from the hit point on a 2D graphics display. A short arrow or no arrow visible would indicate that the hit was substantially parallel to the normal vector of plate 157. Otherwise, the direction of the arrow would indicate the direction in which a golf ball would have been accelerated with respect to the direction of the normal vector of separator plate 157.

FIGS. 18-25 are provided to illustrate a system 400 and an absorber bag 450 for measuring golf swing parameter data upon impact therewith with a club face of a user's golf club according to another embodiment. Unlike the previous embodiment, this embodiment has a thinner bag profile and utilizes accelerometers and/or a turn rate sensor in lieu of velocity sensors to determine golf swing parameter data upon impact.

Figure 18:
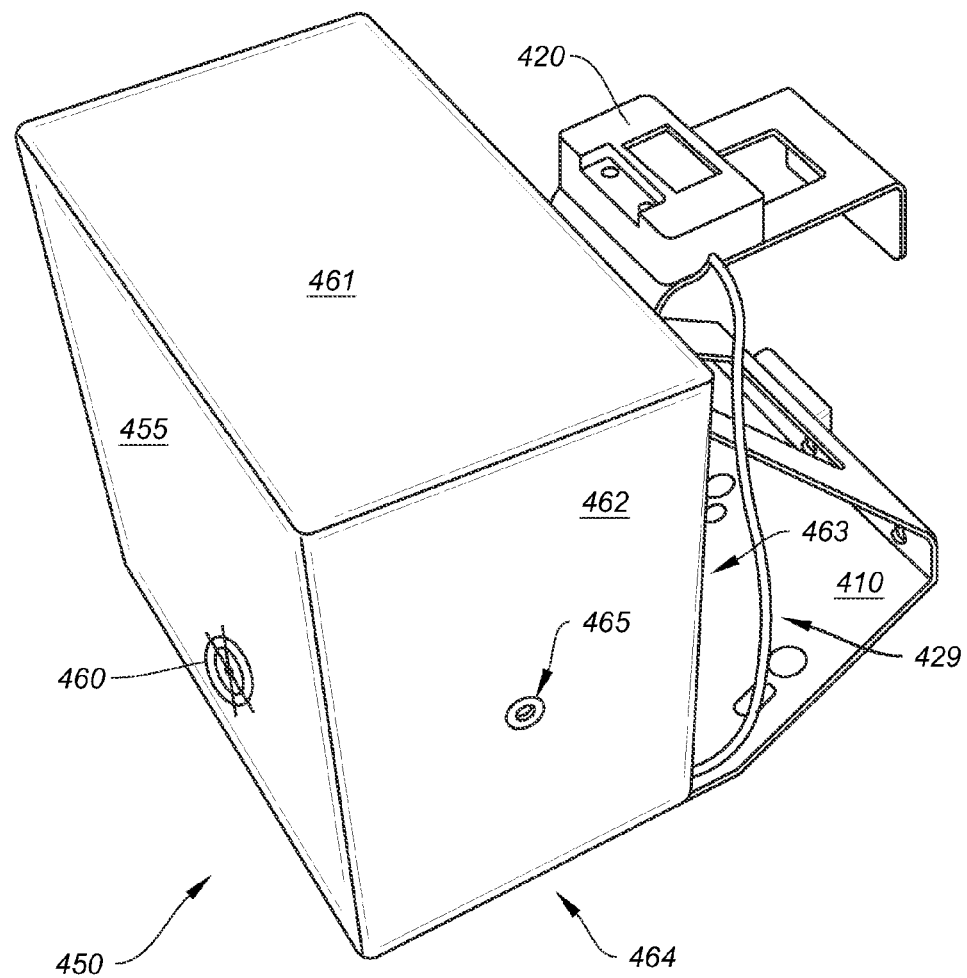
FIG. 18 is a side view of a system for measuring parameter data upon impact with an absorber bag of the system therewith with a club face of a user's golf club, according to another example embodiment.

Referring now generally to FIGS. 18-25, and somewhat similar to impact bag 100, there is shown an absorber bag 450 (FIG. 18) which has a generally cubic shape with an outer construction comprising a plurality of attached resilient panels forming sides, a front facing surface, rear, top and bottom surfaces thereof. As shown in FIG. 18, the front facing surface panel 455 ("front facing surface 455") has a target image 460 imprinted on a lower central portion thereof. The target image 460 is located and oriented for guiding the user's club face thereto for impact therewith. The absorber bag 450 is supported by an anchor frame 410 which is fixedly secured to the ground surface by means such as earth anchors or stakes 417. The anchor frame 410 supports an electronics and display module 420 thereon, with a cable 429 connected between the module 420 and a plurality of sensors embedded within the absorber bag 450 behind target image 460. Module 420 runs analytic software to analyze the measured swing data upon impact of the front surface 455 at target image 460 with a golf club face 475 at a bottom of a downswing of the club by the user (see FIGS. 21, 23, 25, for example) and outputs a tangible result to the user/golfer, such as how hard the golfer struck the absorber bag 450 (as a minimum level of impact measurement), and/or an accuracy/location of the hit on the target image 460, i.e., hit strength and hit accuracy.

The cubic-shaped absorber bag 450 is thus shown anchored directly to the ground surface so as to be fixed in place, and so the front facing surface 455 with target image 460 thereon is impacted by the club face 475 at a bottom of a downswing of the club by the user. The absorber bag 450 further includes a top surface panel 461, side surface panels 462, a rear surface panel 463, and a bottom surface panel 464. (See FIG. 18). These panels may be constructed of a suitable resilient material such as reinforced vinyl, for example, although other resilient materials may be suitable such as leather, canvas and other synthetics. These panels may be attached by suitable stitching, sewing, bound seams, etc. In a particular example, the panels are double stitched for secure integrity and robustness against repeated hits. The panel forming the front facing surface 455 may be formed of an uncoated ballistic nylon material; i.e. a material that is used for bullet proof vests.

Figure 25:
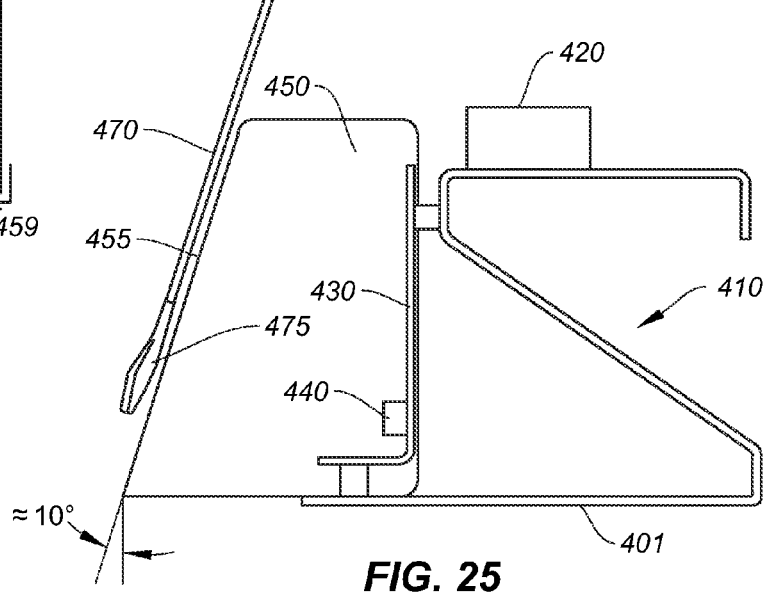
FIG. 25 is a side view of system 400 to show an absorber bag configuration of another example embodiment.

In an alternative construction of the absorber bag 450, the front surface 455 may have an approximate 10 degree sloping angle downward from top to bottom (See FIG. 25). The front surface 455 of the absorber bag 450 may be oriented at 10 degrees to encourage proper shaft lean at impact, as previously noted. Additionally, this angle helps avoid interference of the club shaft 470 with the bag 450 during the last phase of the golf swing, just prior to impact at the bottom of the downswing of the club by the user with the target image 460 on front surface 455.

The sloped front surface 455 in this alternative construction may include the aforementioned target image 460 printed thereon to guide the user to the target area. As briefly discussed previously and above, the absorber bag 450 may be part of a system 400, operatively attached to a processor, such as is in the electronics and display module 420 or a computer system (PC, PDA, laptop, etc) running analytic software to analyze the measured swing data upon impact of the front surface 455 at target image 460 with a golf club face 475 and output a tangible result to the user/golfer, such as how hard the golfer struck the absorber bag 450 (as a minimum level of impact measurement), and/or an accuracy/location of the hit on the target image 460, i.e., hit strength and hit accuracy.

Additionally, and although not shown, the top surface panel 461 of absorber bag 450 may include an opening or access such as a zipper (see as described in FIG. 1, access 135 for impact bag 100 above), so as to allow the user to adjust interior filler/pillow material and access one or more accelerometers therein. Further, there are included a plurality of ventilation holes 465 which may be formed in the top and sides to allow pressure release. The vent holes 465 help displace the air volume in the absorber bag 450, creating less stress on the stitching and the covering material when hitting the bag 450 with a golf club, so as to preserve or extend the bag's life cycle.

Figure 24:
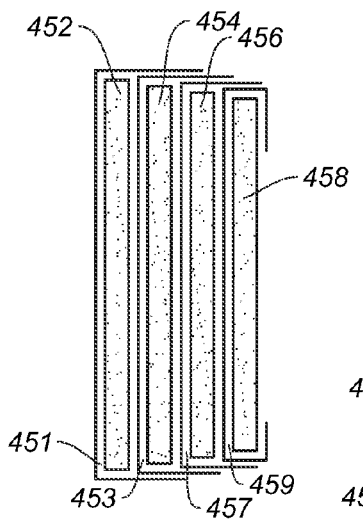
FIG. 24 is a cross-sectional cut of the front section of the interior of absorber bag 450.

FIG. 24 is provided to describe the interior construction of the absorber bag 450, and shows a cross sectional cut. The absorber bag 450 is supported by an accelerated frame 430 which serves as part of the mass element within the interior of the bag 450 and forms the rear section of the interior of bag 450, as shown best in FIG. 21. It in turn is connected to the anchor frame 410 (see FIGS. 18, 19 and 21). The front section of the interior within the absorber bag 450 panel outer casing can be considered as having a "pillow" construction consisting of alternating layers of fabric and open-cell foam. The principle of the bag itself is thus to use successive layers of open cell foam and fabric to absorb most of the kinetic energy stored in the club head arriving on impact with a certain velocity. Naturally, to simulate the position of a golf ball, the target is close to the bottom of the bag or pillow. Repeatedly striking the bag close to the same position again and again and close to the bottom leads to shifting of the open cell foam and fabric layers, in the vicinity of that location, in the upwards direction. The result can be an undesirable change in the absorbing characteristics of the absorber bag 450.

Referring to FIG. 24, and as a measure against this undesirable change, there is provided four (4) pairs of alternating fabric and foam cell layers that make up the front section of the interior of bag 450. The fabric layers 451, 453, 457, and 459 are initially fixed to the alternating open cell foam layers 452, 454, 456, 458 by adhesive. Although four open-cell layers and four fabric layers are shown, there could be greater or fewer than four paired layers of each. Further, a portion of the ends of the fabric layers 451, 453, 457, and 459 extend around the corners for two or more thicknesses of the foam layers (451 and 453, 453 and 457, 457 and 459) and are glued to each other. This arrangement prevents shifting of foam against fabric and anchors the front layers to layers further behind. The contiguous pillow is thus supported within the interior of the absorber bag 450 panel casing by the accelerated frame 430.

The frontal surface of the pillow structure can be made square or rectangular to maintain longevity. A user can extract the fabric/foam pillow from the bag 450 panel outer casing and turn it around to position a yet to be deformed edge to where the target position is of the target image 460 on the front facing surface 455 of bag 450.

Figure 19:
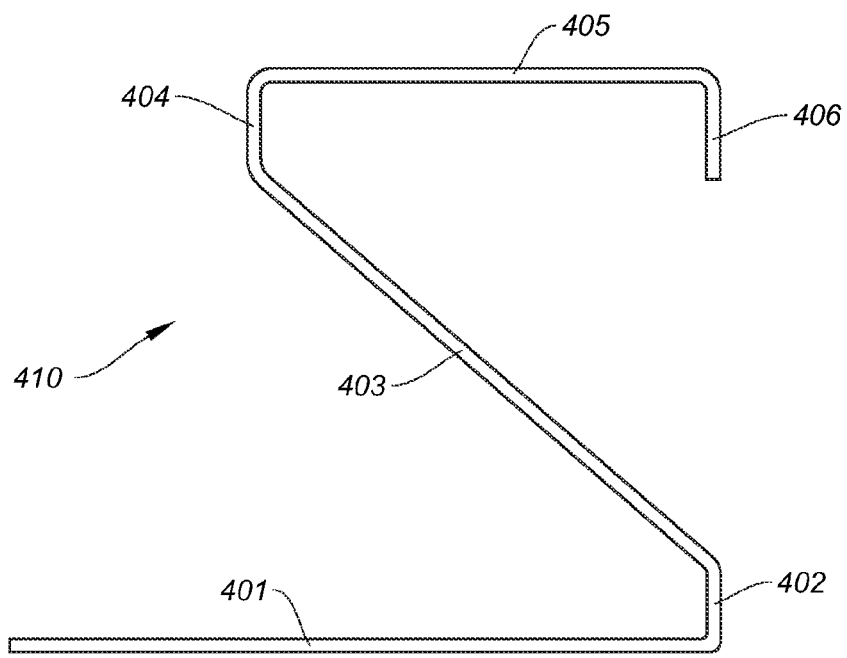
FIG. 19 is a side view of an anchor frame according to another example embodiment.
Figure 20:
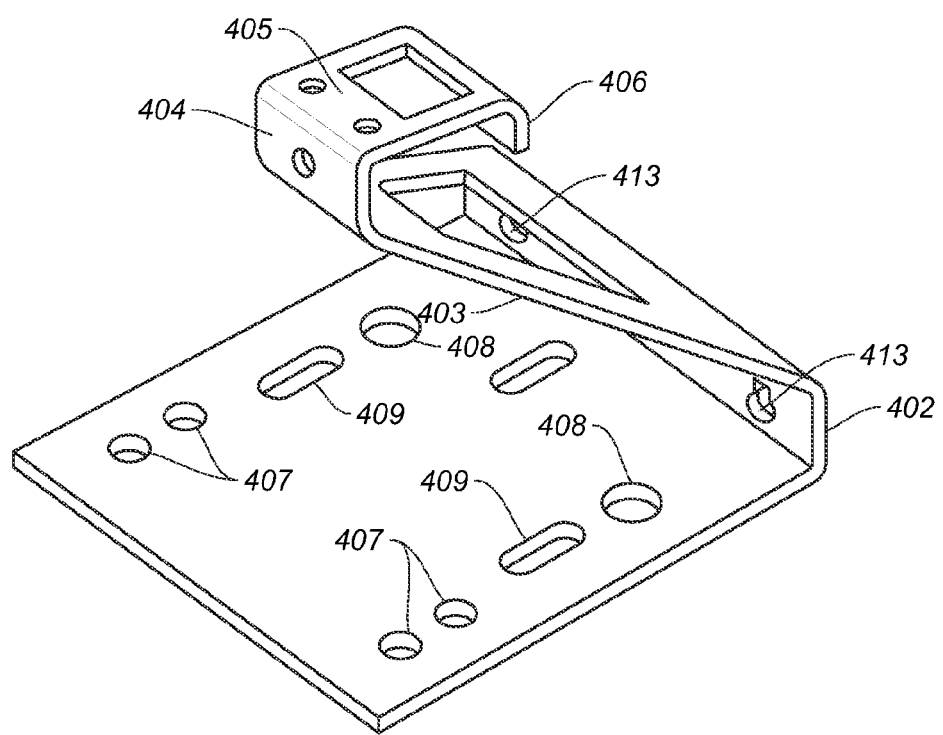
FIG. 20 is a perspective top view of the anchor frame in FIG. 19.
Figure 21:
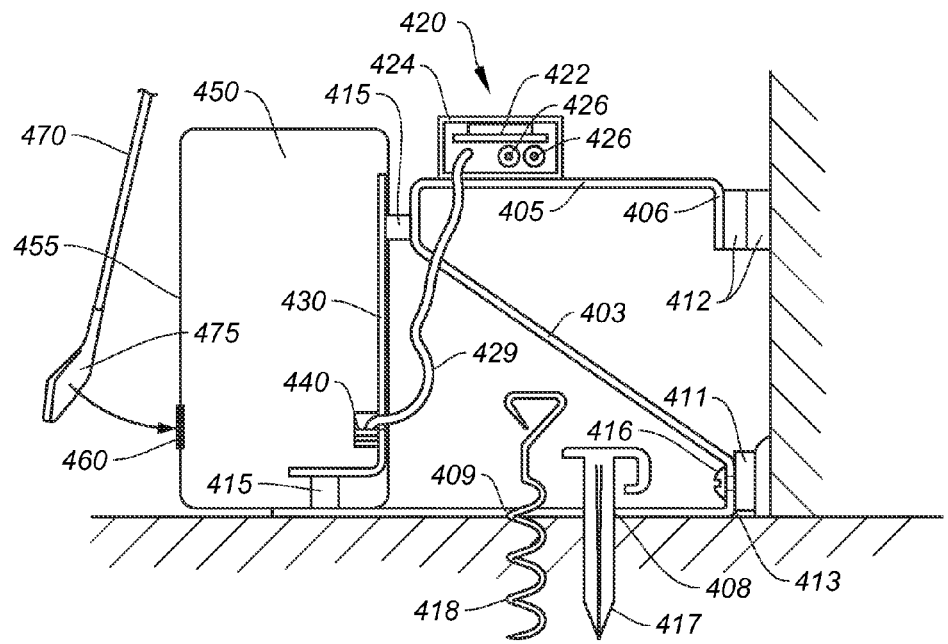
FIG. 21 is a cross-section of the system 400 for measuring golf swing parameter data upon impact with an absorber bag of the system therewith with a club face of a user's golf club, according to another example embodiment.

FIGS. 19 and 20 are provided for illustrating details of an anchor frame according to this embodiment, with FIG. 19 illustrating a side view and FIG. 20 illustrating a perspective top view of the anchor frame. Occasional reference should also be made to FIG. 21, which illustrates a cross-sectional side view of system 400. Referring to FIGS. 19-21, a stationary anchor frame 410 according to this exemplary embodiment of system 400 resembles an "S" shape. Anchor frame 410 may be formed of a suitable metal such as steel, an alloy thereof, aluminum or an alloy thereof, etc. and includes a base floor part 401, a kickboard part 402 for abutting a baseboard or wall, a diagonal part 403, an absorber bag connect part 404, an electronics module/display mount part 405, and a wall support part 406, as illustrated in FIG. 19.

The base floor part 401 is equipped with mounting features 407 for connecting elastic connectors or shock mounts 415 (FIG. 21) to accelerated frame 430, which may be formed of a suitable metal such as steel, an alloy thereof, aluminum or an alloy thereof, etc. In this embodiment, these mounting features 407 may be embodied as simple holes to receive fasteners such as screws to attach elastomeric connectors embodied as three (3) shock mounts 415, which connect the anchor frame 401 to the accelerated frame 430. There can be more than one set of mounting features 407 to set the accelerated frame 430 at different angles against the base floor part 401, as illustrated in FIG. 20.

For outdoor use of system 400 and/or absorber bag 450, a set of circular holes 408 in the base floor part 401 can be used for accommodating straight earth anchors 417 such as those used for pitching tents (FIG. 21). Alternatively, or additionally, a set of elongated holes 409 can accommodate auger type earth anchors 418 that can be wound through these elongated holes 409 into the earth for improved anchoring of system 400 and/or absorber bag 450.

Indoor use of the system 400 and/or absorber bag 450 is facilitated by locating the anchor frame 410 against a wall, whereby the kick board part 402 may rest against a base board, and the wall support part 406 may touch the wall, preventing the absorber bag 450 of system 400 from being dislocated in the direction of a hit with a golf club against the target image 460 on front facing surface 455, as best shown in FIG. 21. Protective elements 411 and 412, which in an example can be fabricated from foam strips with pressure sensitive adhesive films, can be adhered to the kick board part 402 and the wall support part 406, in order to protect wall and base board, and to bridge any offset in the vertical alignment between the face of the base board and the wall. As shown in FIG. 21, displacement of the absorber bag 450 sideways can be prevented by screwing the anchor frame 410 to the baseboard, facilitated by fasteners 416 through keyholes 413 in the kick board part 402.

Figure 22:
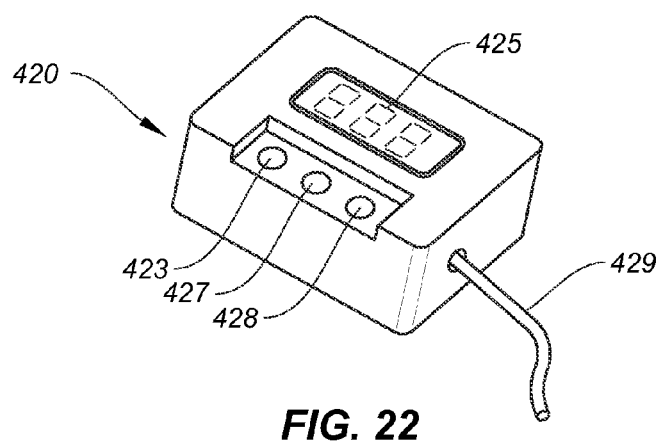
FIG. 22 is a perspective view of an electronics and display control module.

FIGS. 21 and 22 are provided to discuss details about the electronics and display module. Referring to FIGS. 21 and 22, the electronics and display module 420 includes an electronics section 422 (inclusive of a microprocessor and associated firmware), housing 424, and batteries 426, and may be removably mounted to electronics and display mount part 405 of anchor frame 410. The electronics and display module 420 is connected via a cable 429 to a sensor board 440, which is located on the accelerated frame 430.

The primary tasks of the electronics and display module 420 are to condition the analog accelerometer signals, to digitize the signals, to process the signals with the microprocessor and the associated firmware, and to display the results of hit strength and hit location (hit accuracy) on display 425.

Energizing the electronics and display module 420 is by way of batteries 426. Three buttons 423, 427, and 428 are dedicated to allow the user to turn the unit on (423), to turn the unit off (427), and to set the display to show zero (reset button 428). The buttons may be embodied as touch buttons of capacitive sensing technology. This allows the housing 424 to be sealed and (rain) water will not easily penetrate through the housing 424 and interfere with the electronics section 422.

To extend battery life, an auto-shut-off function is implemented, which kicks in after a certain time of no hits having been registered, which puts the electronics and display module 420 into a sleep mode where power consumption is minimal. The display 425 can be of LCD type, OLED type, vacuum fluorescent type, LED type or any other technology. In one example, display 425 is a transflective LCD display, which is easy to read in daylight and can also be backlit when it is dark.

Connected to the electronics and display module 420 via cable 429 are the accelerometer(s) and/or possibly turn rate sensors on sensor board 440. Sensor board 440 is mounted on the accelerated frame 430 in a location that is the intersection of the extended trajectory of a golf club head hitting the target image 460 perpendicularly on the front facing surface 455 of the absorber bag 450 with the surface of the accelerated frame 430.

Figure 23:
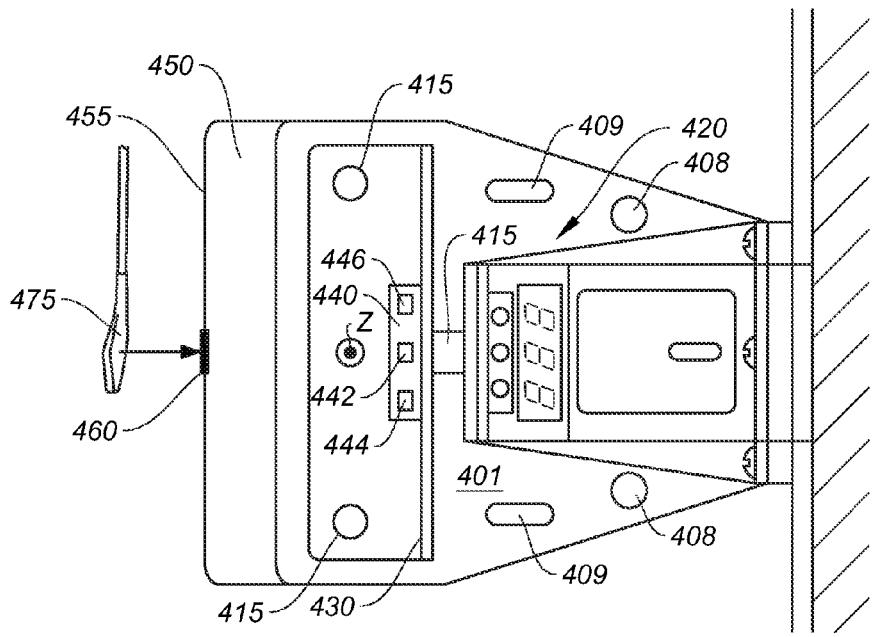
FIG. 23 is a top view of system 400.

FIG. 23 is a top view of the system 400 and is provided to help explain details around the calculations of the golf swing parameters of interest: hit strength and hit accuracy. According to this embodiment, FIG. 23 shows a system in which sensor board 440 has three accelerometers in the z-axis plane, accelerometer 442 directly in line with the target image 460, and accelerometers 444 and 446, parallel to accelerometer 442 in the z-axis plane, laterally off center from the target image 460. From readings accessed from these accelerometer(s) upon impact of a club face 475 with the target image 460, desired swing data is to be fed back to the user on display 425 for review, specifically, the speed of impact or club head speed (hit strength) and accuracy to hit a target spot (i.e., the target image 460) with the club face 475 (hit accuracy).

For the hit strength calculation, the accelerated frame 430 together with absorber bag 450 represents a mass m. The impact force of a golf club head is a result of its momentum change. This impact force first gets dampened by absorber bag 450 and the residual force F accelerates the accelerated frame 430 (F=m×a) against the stationary anchor frame 410 with acceleration a. Force F is reacted by the spring force of the elastomeric shock mounts 415. Thereby the acceleration a, picked up by the accelerometer(s) 442, 444, 446 on sensor board 440 is indicative of the impact and thereby the hit strength of the golfer.

The microprocessor in the electronics section 422 of electronics and display module 420 polls Analog to Digital Converters (ADC) connected to the accelerometer(s) 442, 444, 446. Via the software algorithm in the electronics section 422 of electronics and display module 420, successive values get compared. Increasing and then decreasing values indicate a hit, and the peak value of the value sequence gets recorded, scaled, and indicated on the display 425 as a measure of the hit strength. Knowledge of the club head weight and proper calibration may allow to further deduce the speed of the club head at impact with the front facing surface 455 of the absorber bag 450.

In the described embodiment, the accelerated frame 430 is connected by two shock mounts 415 to the base floor part 401 of the anchor frame 410. The target and the mounting position of the hit strength sensing accelerometer 442 in a hit-strength-only version is midway between the two shock mounts 415. If two accelerometers 444 and 446 are positioned laterally off center from the target image 460 their combined readings sum up as hit strength, whereas the difference between the two accelerometers 444, 446 can be interpreted as the hit location (hit accuracy) in the form of a lateral displacement away from the center. The difference measured between the laterally offset accelerometers 444, 446 amounts to a torque around the z-axis. This torque is reacted by the torque effected by the commensurably deflected shock mounts 415, which are also laterally offset. Dividing the torque by the total impact force gives a lateral distance from the z-axis. This distance can be recorded, scaled and then indicated on display 425 as a hit accuracy value.

The same effect can be deduced by substituting the two laterally offset accelerometers 444, 446 with one single turn rate sensor (not shown) placed at the center behind the target image 460. Hitting the target image 460 dead on will not result in a turning motion around the z-axis, hence an accurate hit. Any lateral offset of the hit location (i.e., at the target image 460) will, however, do so, resulting in a turning motion that is reflective in a loss of hit accuracy. Accordingly, a turn rate sensor (in lieu of accelerometers) may be arranged in an interior of the bag 450 and centered on the rear surface of the bag directly in line with the target image. The turn rate sensor sends signal data to the electronics module 420 upon impact of the club face 475 with the target image 460 on the bag 450, so as to determine a hit strength parameter and a hit accuracy parameter for review by the user.

The analytical software described above may be programmed to operate on, but not limited to the following types of devices/applications: hardware and/or software device specifically designed for the product to capture, display, and analyze the impact information; Email or Personal Websites. The results of the impact could be sent directly to a personal website or email address, to a tablet, smartphone or other PDA device, including, but not limited to, an iPhone, Blackberry, Droid, or other intelligent mobile device platform.

The display methods described herein are to convey the principle only and can take various other forms. Full color graphic displays on PDA's, notebooks, or similar computing devices allow representations of the hit parameters much more intuitively in static or animated form, showing pictures of the golf club hitting a golf ball and the golf ball taking off on a simulated trajectory computed from the hit parameters determined by the apparatus described above. The visual impression may also be supplemented by sound, the loudness and character of which can emulate what is typically heard by real world clubs hitting golf balls, for example.

The sensor technology may also be configured to synchronize via a wireless connection to a smart device and send all the results captured via the sensor from the swing impact. The analytical software may further include a database of 'lessons' to show progress to the golfer.

Although the example embodiments have illustrated selected measurable parameters for display, the systems of the example embodiments may be configured to measure other parameters or metrics based on golf swing impact as well. The digital sensors described herein could be configured to provide very specific metrics in future designs. These include sensors configured so as to be able to discern projected/predicted distance of the golf ball, predicted 'straightness' of the golf ball trajectory, as well as to read shaft lean, de-lofting the face, and face angle (open, square, or closed and how many degrees) at impact. This information and/or display output interface with software could be sold as an application for one's smart phone, for example.

The example embodiments being thus described, it will be obvious that the same may be varied in many ways. For example, instead of digital sensors, mechanical sensors could be employed. In a mechanical-based system, with a pressure gage only hooked up to the sensor(s) embedded in the impact bag 100/absorber bag 450, the mechanical-based sensors would provide a feedback in pounds as to the force of impact on the gage at which the golf club struck the target surface.

Accordingly, mechanical sensors would not require any electronic data capturing devices and/or software. The mechanical sensors would be inserted into the sensor pouch and then connected to a direct pressure gauge. The gauge could be reset after every hit. The gauge would be capable of measuring the impact force. Such variations are not to be regarded as departure from the example embodiments, and all such modifications as would be obvious to one skilled in the art are intended to be included in the following claims.

We claim:

1. A system for measuring golf swing parameter data on impact of a club face of a user's golf club with a target surface, comprising:
    an absorber bag having a front facing surface with target image thereon for receiving an impact of the user's club face therewith,
    an anchor frame to which the bag is fixedly and immovably attached thereto,
    an electronics module removably attachable to the anchor frame,
    a plurality of shock mounts positioned between the absorber bag and anchor frame to fix the absorber bag to the anchor frame, and
    at least one accelerometer in electrical communication with the electronics module and arranged on a rear surface of the bag that measures acceleration upon impact of the club face with the absorber bag, providing a signal that is converted by the electronics module into golf swing parameter data for display to the user.

2. The system of claim 1, wherein the golf swing parameter data includes a hit strength value indicative of how hard the user hit the front facing surface of the absorber bag with the club face.

3. The system of claim 1, wherein the golf swing parameter data includes a hit accuracy determination indicative of how close to a target image the club face landed on impact.

4. The system of claim 1, wherein
    the absorber bag is configured in a generally cubic outer shape with an outer construction comprising a plurality of attached resilient panels forming sides, the front facing surface with target image thereon, a rear surface, a top surface and a bottom surface thereof, the cubic-shaped absorber bag anchored directly to a ground surface so as to be fixed in place, and so the front facing surface with target image thereon is impacted by the club face at a bottom of a downswing of the club by the user.

5. The system of claim 1, wherein the anchor frame is configured to be attached to a wall surface and a baseboard via a plurality of protective foam elements.

6. The system of claim 1, further comprising an accelerated frame part attached to a rear interior surface of the absorber bag so that the shock mounts are arranged between the accelerated frame part and anchor frame, the accelerated frame part supporting the absorber bag thereon and including the at least one accelerometer attached thereto.

7. The system of claim 1, wherein the anchor frame is staked to a ground surface.

8. The system of claim 1, wherein the absorber bag includes
an interior including:
a plurality of alternating layers of fabric and open-cell foam in adjacent stacked
relation arranged as a front section of the interior, and
a metal frame as a back section of the interior.

9. The system of claim 1, further comprising a sensor board arranged on a rear interior surface of the bag with a plurality of accelerometers thereon sending acceleration signal data to the electronics module upon impact of the club face with the bag so as to determine a hit strength parameter and a hit accuracy parameter for review by the user.

10. The system of claim 1, further comprising a turn rate sensor arranged in an interior of the bag and centered on the rear surface of the bag directly in line with the target image, the turn rate sensor sending signal data to the electronics module upon impact of the club face with the target image on the bag so as to determine a hit strength parameter and a hit accuracy parameter for review by the user.

11. An absorber bag for measuring golf swing parameter data upon impact therewith with a club face of a user's golf club, comprising:
an outer construction composed of a plurality of resilient panels arranged in a generally cubic shape with a front facing surface with a target image thereon for receiving the user's club face thereto for impact therewith, the absorber bag fixedly attached to a ground surface in an immovable state,
an electronics module,
an interior including:
a plurality of alternating layers of fabric and open-cell foam in adjacent stacked relation arranged behind the front facing surface as a front section of the interior,
a frame as a rear section of the interior, and
one or more accelerometers in electrical communication with the electronics module and positioned on the frame,
the one or more accelerometers measuring acceleration upon impact of the club face with the bag, providing signals that are converted by the electronics module into golf swing parameter data for display to the user.

12. The absorber bag of claim 11, wherein the golf club swing data includes a hit strength value indicative of how hard the user hit the front facing surface of the absorber bag with the club face.

13. The absorber bag of claim 11, wherein the golf club swing data includes a hit accuracy determination indicative of how close to a target image the club face landed on impact.

14. The absorber bag of claim 11, wherein the cubic-shaped absorber bag is anchored directly to a ground surface so as to be fixed in place, and so the front facing surface with target image thereon is impacted by the club face at a bottom of a downswing of the club by the user.

15. A system for measuring golf swing parameter data on impact of a club face of a user's golf club with a target surface, comprising:
an absorber bag having a front facing surface for receiving an impact thereon with the club face, the absorber bag anchored directly to a ground surface so as to be fixed in place and immovable, so the front facing surface of the fixed absorber bag is impacted by the club face at a bottom of a downswing of the club by the user,
at least one accelerometer that measures acceleration upon impact of the club face with the front facing surface, and
a processor connected to the accelerometer for receiving the acceleration data and determining golf swing parameter data related to the impact.

16. The system of claim 15, wherein the determined golf swing parameter data includes a hit strength value indicative of how hard the user hit the front facing surface of the absorber bag with the club face.

17. The system of claim 15, wherein the determined golf swing parameter data includes a hit accuracy determination indicative of how close to a target image on the front facing surface the club face landed on impact.

18. The system of claim 15, further comprising
an anchor frame,
a pair of shock mounts attaching a lower part of the absorber bag to the anchor frame,
an accelerated frame part attached to a rear surface of the absorber bag so that the shock mounts are arranged between the accelerated frame part and anchor frame, the accelerated frame part supporting the absorber bag thereon and including the at least one accelerometer attached thereto.

19. The system of claim 18, wherein the anchor frame includes:
a base with apertures therein for receiving stakes to secure it to an outdoor ground surface, and
foam protective elements for securing the anchor frame against a wall and baseboard indoors.

20. The system of claim 15, further comprising a sensor board arranged on a rear interior surface of the bag with a plurality of accelerometers thereon sending acceleration signal data to the processor upon impact of the club face with the bag so as to determine a hit strength parameter and a hit accuracy parameter for review by the user.

* * * * *